US008962697B2

(12) United States Patent
Laronde et al.

(10) Patent No.: US 8,962,697 B2
(45) Date of Patent: Feb. 24, 2015

(54) BIOREPONSIVE POLYMERS

(75) Inventors: Frank Laronde, Toronto (CA); Hanje Chen, Toronto (CA)

(73) Assignee: Interface Biologics Inc., Toronto (CA)

( * ) Notice: Subject to any disclaimer, the term of this patent is extended or adjusted under 35 U.S.C. 154(b) by 1238 days.

(21) Appl. No.: 12/308,800

(22) PCT Filed: Jun. 29, 2007

(86) PCT No.: PCT/IB2007/004228
§ 371 (c)(1),
(2), (4) Date: Sep. 9, 2009

(87) PCT Pub. No.: WO2008/053362
PCT Pub. Date: May 8, 2008

(65) Prior Publication Data
US 2010/0041771 A1   Feb. 18, 2010

Related U.S. Application Data

(60) Provisional application No. 60/817,822, filed on Jun. 30, 2006.

(51) Int. Cl.
*A61K 47/48*    (2006.01)
*C08L 77/00*    (2006.01)

(52) U.S. Cl.
CPC ..... *A61K 47/48238* (2013.01); *A61K 47/48169* (2013.01); *A61K 47/48176* (2013.01); *A61K 47/4823* (2013.01); *A61K 47/48338* (2013.01); *C08L 77/00* (2013.01)
USPC ......... 514/772.4; 514/418; 514/777; 514/781

(58) Field of Classification Search
USPC ............... 514/772.4, 418, 781, 777
See application file for complete search history.

(56) References Cited

U.S. PATENT DOCUMENTS

| | | | |
|---|---|---|---|
| 3,929,992 A | 12/1975 | Sehgal et al. | |
| 5,362,718 A | 11/1994 | Skotnicki et al. | |
| 5,665,772 A | 9/1997 | Cottens et al. | |
| 2004/0228831 A1* | 11/2004 | Belinka et al. | 424/78.27 |
| 2005/0063937 A1* | 3/2005 | Li et al. | 424/78.27 |
| 2005/0255079 A1* | 11/2005 | Santerre et al. | 424/78.3 |

FOREIGN PATENT DOCUMENTS

| | | | | |
|---|---|---|---|---|
| CA | 2369999 | | 11/2000 | |
| CA | 2419429 | | 3/2002 | |
| CA | 2462529 | | 12/2002 | |
| CA | 2506319 | | 6/2004 | |
| CA | 2467321 | | 11/2005 | |
| JP | 2003034653 | A | 2/2003 | |
| WO | WO 00/64486 | * | 11/2000 | ............. A61K 47/48 |
| WO | WO-02098477 | A2 | 12/2002 | |
| WO | WO-2005110485 | A1 | 11/2005 | |
| WO | WO 2007/100883 | | 9/2007 | |

OTHER PUBLICATIONS

Kim et al., "Controlled Release of Prodrugs Based on the Biodegradable Poly(L-glutamic acid) Microspheres," *Polymer Journal.* 31(10): 813-816 (1999).
Pechar et al., "Poly(ethylene glycol) Multiblock Copolymer as a Carrier of Anti-Cancer Drug Doxorubicin," *Bioconjugate Chemistry.* 11(2): 131-139 (2000).
International Search Report (PCT/IB2007/004228), dated Jul. 30, 2008.
Written Opinion of the International Searching Authority (PCT/IB2007/004228), dated Jul. 30, 2008.
New Zealand Patent Office Communication (New Zealand Application No. 574077), dated Aug. 18, 2010.
International Preliminary Report on Patentability (PCT/IB2007/004228), dated Jan. 25, 2011.
Alves, et al. "S3 to S3' subsite specificity of recombinant human cathepsin K and development of selective internally quenched fluorescent substrates" Biochem J. 373(Pt 3):981-6 (2003).
McAlpine et al., "Revised NMR assignments for rapamycin," J Antibiodics. 44(6):688-90 (1991).
Pagano TG. "Complete assignments of the 1H and 13C resonances of 40-epi-(N1-tetrazolyl)-rapamycin and revised 13C assignments for rapamycin" Magn Reson Chem. 43(2):174-5 (2005).
Putnam et al. "Primary structure of a human IgA1 immunoglobulin. IV. Streptococcal IgA1 protease, digestion, Fab and Fc fragments, and the complete amino acid sequence of the alpha 1 heavy chain" J Biol Chem. 254(8):2865-74 (1979).
Van Duyne et al., "Atomic structure of the rapamycin human immunophilin FKBP-12 complex," J Am Chem Soc. 113(13):7433-34 (1991).
Pechar et al., "Poly(ethylene glycol) Multiblock Copolymer as a Carrier of Anti-Cancer Drug Doxorubicin," *Bioconjug. Chem.*11(2): 131-139, 2000.
Notice of Reasons for Rejection in Japanese Application No. 2009-517485 mailed Jul. 3, 2012.

* cited by examiner

*Primary Examiner* — Anoop Singh
*Assistant Examiner* — Anna Falkowitz
(74) *Attorney, Agent, or Firm* — Clark & Elbing LLP; Kristina Bieker-Brady

(57) ABSTRACT

The invention features biodegradable polymers for the delivery of biologically active agents. The polymers include at least one biologically active agent covalently attached via a polyamide linker susceptible to selective hydrolysis by peptidase enzymes. Hydrolysis of the polyamide linker releases the biologically active agent in vivo.

19 Claims, No Drawings

BIORESPONSIVE POLYMERS

CROSS-REFERENCE TO RELATED APPLICATIONS

This application is the U.S. National Stage of International Application No. PCT/IB32007/004228, filed Jun. 29, 2007, which in turn, claims the benefit of U.S. Provisional Application No. 60/817,822, filed Jun. 30, 2006, each of which is incorporated by reference.

BACKGROUND OF THE INVENTION

The invention relates to methods and compositions for the sustained release delivery of biologically active agents.

Polymeric materials have been widely used for manufacturing of medical devices, such as artificial organs, implants, medical devices, vascular prostheses, blood pumps, artificial kidney, heart valves, pacemaker lead wire insulation, intraaortic balloon, artificial hearts, dialyzers and plasma separators, among others. The polymer used within a medical device must be biocompatible (e.g., must not produce toxic, allergic, inflammatory reactions, or other adverse reactions). It is the physical, chemical and biological processes at the interface, between the biological system and the synthetic materials used, which defines the short- and long-term potential applications of a particular device. In general, the exact profile of biocompatibility and biodegradation, including chemical and physical/mechanical properties i.e., elasticity, stress, ductility, toughness, time dependent deformation, strength, fatigue, hardness, wear resistance, and transparency for a biomaterial are extremely variable.

The polymeric coating of a medical device may also serve as a repository for delivery of a biologically active agent. Where the active agent is a pharmaceutical drug, it is often desirable to release the drug from the medical device over an extended period of time. Most systems for kinetically controlled direct drug delivery employ a polymer. For example, the agent may be released as the polymer enzymatically degrades or disintegrates in the body or may diffuse out of the polymeric matrix at a controlled rate. A site-specific drug transfer system can produce a high concentration of agent at the treatment site, while minimizing the adverse effects associated with systemic administration.

A polymeric system being used to control release of the drug must be free of impurities that trigger adverse biological responses (i.e., biologically inert), must produce the desired release profile, and must possess the mechanical properties required of the medical device.

In most cases biologically active agents are simply mixed with a polymer platform in a suitable solvent system. The biologically active agent is then released by particle dissolution or diffusion (when the non-bioerodable matrices are used) or during polymer breakdown (when a biodegradable polymer is used). In such systems the biologically active agents are released without regard to biological function or condition of the tissue at the site of implantation.

It is desirable to design a polymeric system which responds to a biological function or condition of the tissue at the site of implantation.

SUMMARY OF THE INVENTION

The invention features biodegradable polymers for the delivery of biologically active agents. The polymers include at least one biologically active agent covalently attached to the polymer via a polyamide linker susceptible to hydrolysis by peptidase enzymes. Hydrolysis of the polyamide linker releases the biologically active agent in vivo.

In a first aspect, the invention features a biodegradable polymer having a repeating unit including a biologically active agent covalently attached to a biologically responsive polyamide linker susceptible to selective hydrolysis by a peptidase enzyme, wherein the polymer releases the biologically active agent in vivo in response to the hydrolysis, and wherein the polymer is greater than 5 kDa. In embodiments of the above aspect, the polymer is greater than 10 kDa, 20 kDa, 40 kDa, 80 kDa, 100 kDa, 200 kDa, 500 kDa, or even 1,000 kDa.

In particular embodiments, the polymer is further described by formulas I or II:

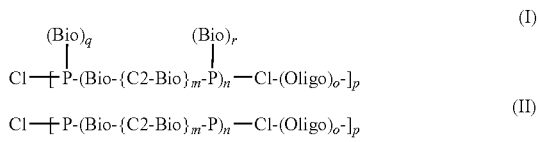

In formulas I and II, each Bio is, independently, one or more biologically active agents, or precursors thereof, tethered to polyamide linker P through hydrolysable covalent bonds; each P is a polyamide linker susceptible to hydrolysis by a peptidase enzyme and tethered to the Bio and C1; C1 is a coupling segment linking P to Oligo; C2 is a hydrolysable coupling segment or a polyamide linker susceptible to hydrolysis by a peptidase enzyme linking Bio to Bio; Oligo is a short length of polymer segment having a molecular weight of less than 5,000 Da and including less than 100 monomeric repeating units; each of n, o, and p is independently an integer greater than 0; m is an integer 0 or 1; and each of q and r is independently an integer 0 or greater. In certain embodiments, C1 includes ethylene glycol, butane diol, hexane diol, hexamethylene diol, 1,5 pentanediol, 2,2-dimethyl-1,3 propanediol, 1,4-cyclohexane diol, 1,4-cyclohexanedimethanol, tri(ethylene glycol), poly(ethylene glycol), poly(ethylene oxide)diamine, lysine esters, silicone diols and diamines, polyether diols and diamines, carbonate diols and diamines, dihydroxy vinyl derivatives, dihydroxy diphenylsulfone, ethylene diamine, hexamethylene diamine, 1,2-diamino-2 methylpropane, 3,3,-diamino-n-methyldipropylamine, 1,4 diaminobutane, 1,7 diaminoheptane, or 1,8 diaminooctane moieties. In still another embodiment, C1 is covalently tethered to Oligo by via urethanes, esters, ureas, sulfonamides, ether, amine, carbon-carbon, carbomates, anhydrides, or amides linkages. In other embodiments, C2 is a polyamide linker susceptible to hydrolysis by a peptidase enzyme or a coupling segment which is non-selectively hydrolysable.

In a related aspect, the invention features a polymer including a pendant group, the pendant group including a biologically active agent covalently attached to a biologically responsive polyamide linker susceptible to selective hydrolysis by a peptidase enzyme, wherein the biologically responsive polyamide linker is covalently attached to the polymer and the polymer releases said biologically active agent in vivo in response to the hydrolysis.

In particular embodiments, the polymer is further described by formula III:

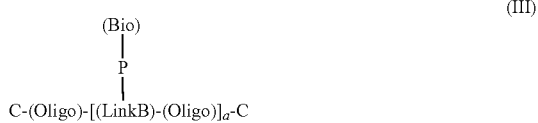

In formula III, each Bio is, independently, one or more biologically active agents, or precursors thereof, tethered to polyamide linker P through hydrolysable covalent bonds; each P is a polyamide linker susceptible to hydrolysis by a peptidase enzyme and tethered to the Bio and LinkB; C is a chain terminating group; Oligo is an oligomeric segment; LinkB is a coupling segment; and a is an integer greater than 0. In certain embodiments, C is a surface active group selected from polydimethylsiloxanes, hydrocarbons, polyfluoroalkyls, fluorinated polyethers, polyalkylene oxides, and combinations thereof. Desirably, C is a polyfluoroalkyl having a molecular weight of between 100-1,500 Da. Polyfluoroalkyls that can be used include, for example, radicals of the general formula $CF_3(CF_2)_rCH_2CH_2$— wherein r is 2-20, and $CF_3(CF_2)_s(CH_2CH_2O)_\chi$ wherein $\chi$ is 1-10 and s is 1-20. In other embodiments, the polymer of formula III includes an Oligo having an absolute molecular weight of less than about 2 kDa and a is less than 10. Desirably, the Oligo has an absolute molecular weight of less than about 15 kDa, 14 kDa, 13 kDa, 12 kDa, 11 kDa, 10 kDa, 8 kDa, 6 kDa, 4 kDa, or even 1 kDa.

In certain embodiments of any of the above aspects, Oligo includes polyurethane, polyurea, polyamides, polyaklylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethylene oxide, or polyethylenebutylene segments. Desirably, Oligo has a molecular weight of less than 15,000 Da.

In another embodiment of the above aspects, P is tethered to Bio by a carboxylic ester, amide or sulfonamide linkage, provided at least one link is an amide linkage. In another embodiment, each P is an independent polyamide linker of 2-60 amino acids.

In yet another embodiment of the above aspects, Bio is one or more biologically-active entities selected from carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, vitamins, lipids, and prodrugs thereof. Desirably, the Bio is one or more anti-inflammatory agents or antibiotic agents.

The polymers of the invention are designed for selective hydrolysis in the presence of a peptidase enzyme. The peptidase enzyme can be selected from, without limitation, endopeptidases (e.g., matrix metalloproteinases, such as MMP-1, MMP-2, MMP-3, MMP-8, MMP-9, MMP-10, MMP-11, and MMP-13), exopeptidases (e.g., carboxypeptidases and aminopeptidases). The peptidase can be one produced by a parasitic organism, such as *Staphylococcus* spp. or *C. albicans*. In one particular embodiment the peptidase enzyme is cathepsin K.

The invention also features a polymer of the invention blended with a compatible base polymer. Base polymers that can be used in combination with the polymers of the invention include, without limitation, polyurethanes, polysulfones, polycarbonates, polyesters, polyethylene, polypropylene, polystyrene, polysilicone, poly(acrylonitrile-butadienestyrene), polybutadiene, polyisoprene, polymethylmethacrylate, polyamine, polyvinylacetate, polyacrylonitrile, polyvinyl chloride, polyethylene, terephthalate, cellulose and other polysaccharides.

The invention features a shaped article including a polymer of the invention blended with a compatible base polymer.

The invention further features a shaped article including a polymer of the invention.

Shaped articles of the invention can be in the form of an implantable medical device (e.g., a cardiac-assist device, a catheter, a stent, a prosthetic implant, a suture, a cuff, a mesh, a hernia patch, a wound dressing, a bandage, an artificial sphincter, or a drug delivery device), self-supporting film, or fiber.

The invention also features a method of reducing inflammation at a site in a mammal in need thereof by implanting an article of the invention at the site, wherein the article includes an anti-inflammatory agent which is released from the surface of the article in response to selective hydrolysis by peptidases expressed during inflammation in an amount sufficient to reduce inflammation.

The invention also features a method of reducing restenosis at a site in a mammal in need thereof by implanting an article of the invention at the site, wherein the article includes an anti-proliferative agent which is released from the surface of the article in response to selective hydrolysis by peptidases expressed during proliferation in an amount sufficient to reduce restenosis.

In another aspect, the invention features a method of reducing pain at a site in a mammal in need thereof by implanting an article of the invention at the site, wherein the article includes an analgesic or anesthetic agent which is released from the surface of the article in response to selective hydrolysis by peptidases expressed during pain in an amount sufficient to reduce pain.

In still another aspect, the invention features a method of relaxing muscle at a site in a mammal in need thereof by implanting an article of the invention at the site, wherein the article includes an antispasmodic agent which is released from the surface of the article in response to selective hydrolysis by peptidases expressed during muscle spasm in an amount sufficient to relax muscle.

By "oligomeric segment" is meant a relatively short length of a repeating unit or units, generally less than about 50 monomeric units and molecular weights less than 10,000 but preferably <5000. Preferably, [Oligo] is selected from the group consisting of polyurethane, polyurea, polyamides, polyalkylene oxide, polycarbonate, polyester, polylactone, polysilicone, polyethersulfone, polyolefin, polyvinyl, polypeptide, polysaccharide; and ether and amine linked segments thereof.

By "surface active group" is meant a lipophilic group covalently tethered to a surface modifier. The surface active group can be positioned to cap one or both termini of the central polymeric portion of the surface modifier or can be attached to one or more side chains present in the central polymeric portion of the surface modifier. Examples of surface active groups include, without limitation, polydimethylsiloxanes, hydrocarbons, fluorocarbons, fluorinated polyethers, polyalkylene oxides, and combinations thereof.

As used herein, "LinkB" refers to a coupling segment capable of covalently linking two oligo moieties and a biologically responsive polyamide linker. Typically, linkB molecules have molecular weights ranging from 40 to 700. Preferably the linkB molecules are selected from the group of functionalized diamines, diisocyanates, disulfonic acids, dicarboxylic acids, diacid chlorides and dialdehydes, wherein the functionalized component has secondary functional chemistry that is accessed for chemical attachment of a surface active group. Such secondary groups include, for example, esters, carboxylic acid salts, sulfonic acid salts, phosphonic acid salts, thiols, vinyls and secondary amines. Terminal hydroxyls, amines or carboxylic acids on the oligo intermediates can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines.

As used herein, "C" refers to a chain terminating group. Exemplary chain terminating groups include monofunctional groups containing an amine, alcohol, or carboxylic acid functionality. Chain terminating groups can include, for example, surface active groups.

By "coupling segment" is meant a molecule or chemical bond covalently linking segments together in the bioresponsive polymer. Typically, coupling segments can have molecular weights ranging from 16 to 2000 Da and have multi-functionality, but preferably di-functionality, to permit coupling of two segments. The coupling segments can be synthesized from the groups of precursor monomers selected from diols, diamines and/or a compounds containing both amine and hydroxyl groups. Precursors that can be incorporated into coupling segments include, without limitation, ethylene glycol, butane diol, hexane diol, hexamethylene diol, 1,5 pentanediol, 2,2-dimethyl-1,3 propanediol, 1,4-cyclohexane diol, 1,4-cyclohexanedimethanol, tri(ethylene glycol), poly(ethylene glycol), poly(ethylene oxide)diamine, lysine esters, silicone diols and diamines, polyether diols and diamines, carbonate diols and diamines, dihydroxy vinyl derivatives, dihydroxy diphenylsulfone, ethylene diamine, hexamethylene diamine, 1,2-diamino-2 methylpropane, 3,3-diamino-n-methyldipropylamine, 1,4 diaminobutane, 1,7 diaminoheptane, or 1,8 diaminooctane.

By "biologically active agent" is meant a molecule that can be coupled to a polyamide linker via a hydrolysable covalent bond. The biologically active agent is selected for some specific and intended physical, pharmacological, or biological action. Typically the biologically active agent has a molecular weight ranging from 40 to 2,000 Da. Biologically active agents that can be used in the methods and compositions of the invention include, without limitation, anti-inflammatory, anti-oxidant, anti-coagulant, anti-microbial (i.e. fluoroquinolones), cell receptor ligands, and bio-adhesive molecules (e.g., oligosaccharides, oligonucleic acid sequences for DNA and gene sequence bonding, and phospholipid head groups to provide cell membrane mimics). Desirably, the biologically active agent is a compound useful for the therapeutic treatment of a plant or animal when delivered to a site of diseased tissue. Alternatively, the biologically active agent can be selected to impart non-therapeutic functionality to a surface. Such agents include, for example, pesticides, bactericides, fungicides, fragrances, and dyes.

By "amount sufficient" is meant the amount of biologically active agent necessary to achieve a desired result. The amount sufficient will vary depending upon a variety of parameters, including the condition being treated (e.g., pain or microbial growth, among others), the site being treated, the biologically active agent selected, and the delivery vehicle employed (e.g., implanted device, cream, or pellet, among others). A sufficient amount can be determined for any given set of conditions using standard methods. For example, the release of biologically active agent from a surface can be monitored as a function of the parameters above. Based upon these results, a vehicle prepared which releases the agent at a rate that produces the desired effect.

By "polyamide linker" is meant a biologically responsive polyamide sequence containing specific cleavage recognition sites for peptidase enzymes. The sequences are susceptible to hydrolysis by endopeptidases and exopeptidases and are hydrolyzed to form polymer fragments including a biologically active agent when such enzymes are present. The polyamide linker is stable in the absence of peptidase enzymes.

By "base polymer" is meant a polymer having a tensile strength of from about 350 to about 10,000 psi, elongation at break from about 300% to about 1500%, an unsupported thickness of from about 5 to about 100 microns, and a supported thickness of from about 1 to about 100 microns.

By "prodrug" is meant a precursor to a biologically active agent that is converted in vivo, e.g., by enzymatic and/or hydrolytic mechanisms, into a biologically active agent. Prodrugs include, without limitation, esterified biologically active agents.

As used herein, "susceptible to selective hydrolysis" refers to an increase in the rate of hydrolysis observed for a polymer of the invention incorporating a polyamide designed to be hydrolyzed in response to the presence of one or more peptidase enzymes. A polyamide-containing polymer of the invention is susceptible to selective hydrolysis if the rate of hydrolytic degradation observed for the polymer in whole blood at physiological pH and temperature, optionally with the addition of a target peptidase enzyme (i.e., a peptidase enzyme which recognizes and cleaves the polyamide) in a physiologically relevant concentration, is greater than 5, 10, 15, 20, 30, or 40 times the degradation rate observed under the same conditions for an otherwise identical polymer system in which the polyamide is replaced by a non-selective polyamide sequence, such as SEQ ID NOS. 1 and 2, below.

VFFRRQTA        (SEQ ID NO. 1)

PRRICV          (SEQ ID NO. 2)

The polyamide of SEQ ID NOS. 1 and 2 are not selectively recognized by peptidase enzymes and, therefore, the rate of hydrolysis for a polymer containing these non-selective sequences under any given set of conditions is a measure of the rate of non-selective hydrolysis.

By "endopeptidase" is meant an enzyme that breaks peptide bonds between amino acids of a polypeptide or a polyamide chain.

By "exopeptidase" is meant an enzyme that catalyses the removal of an amino acid from the carboxy- or amino-terminus of a polypeptide or polyamide chain.

Other features and advantages of the invention will be apparent from the following Detailed Description and the claims.

DETAILED DESCRIPTION

The methods and compositions of the invention feature a pharmaceutically-active polymer for the delivery of biologically active agents. The invention includes one or more biologically active agents covalently tethered between one or more biologically responsive polyamide linkers further tethered to oligomeric segments that prevent the release or diffusion of the biologically active agents. The polyamide linker contains specific peptidase cleavage sites that are susceptible to hydrolysis in the presence of peptidase enzymes. The biologically active agents are released from the oligomeric segment during a physiological or pathological process that causes an upregulation of peptidase activity. For example, an immune response that elicits macrophage release of endopeptidases can hydrolyze the polyamide linker to release smaller polyamide fragments containing the biologically active agent. Alternatively, an invading microorganism may secrete proteolytic enzymes that can also hydrolyze the polyamide linker. Further hydrolysis by exopeptidases completely frees the biological agent from tethered polyamide or individual amino acids.

Biological Response

Release of biologically active agents from the oligomeric segment can, for example, be in response to peptidase enzymes that are upregulated during a physiological response or pathological process. For example, during a typical immune response, macrophages release proteases such as matrix metalloproteinases (MMP) and serine proteinases (SP). The matrix metalloproteinases represent a family of zinc-dependent endopeptidase enzymes involved in normal and disease related tissue remodeling, and include MMP-1, MMP-2, MMP-3, MMP-8, MMP-9, MMP-10, MMP-11, and MMP-13. They are expressed at low levels in normal adult tissues but are upregulated during physiological and pathological processes, such as endometrial cycling, wound healing, liver, cirrhosis, or cancer invasion. Among this family of MMPs, three are up-regulated particularly during inflammatory responses, namely MMP-1, MMP-2, and MMP-9. MMP-2 and MMP-9 differ from other MMPs because they contain three fibronecton type II repeats that have high binding affinity for collagen. Fibroblast, endothelial cells, and epithelial cells (e.g. non-inflammatory cells) secrete mainly MMP-1, MMP-2 (gelatinase-A) and/or MMP-9 (gelatinase-B), whereas polymorphonuclear neutrophils (PMNs) and alveolar macrophages (e.g. inflammatory cells) release mainly MMP-8 and MMP-9.

Alternatively, the release of biologically active agents from the oligomeric segment can be in response to proteolytic enzymes released by invading microorganisms. A large number of prokaryotic organism ubiquitously secrete proteolytic enzymes. In most cases they are involved in nutrient acquisition but pathogenic bacteria may also release peptidases as virulence factors. Moreover, Staphylococci, in particular, *Staphylococcus aureus*, are known to produce several extracellular proteases, including serine- and cysteine-proteases, and metalloenzymes. In vitro studies show that during early growth phase of *Staphylococcus*, surface proteins, functioning mainly as adhesion factors, are suppressed and the production of certain proteins intensifies. Secretion of bacterial proteases is regulated by gene expression, wherein the bacterial chromosome is organized into four distinct operons: the staphylococcal serine protease (ssp) operon; serine protease like proteins operon (spl); Staphylococcal cysteine protease (scp) operon; and the gene for aureolysin (aur). Proteolytic enzymes that are up-regulated in the late stages of bacterial growth include *Staphylococcus aureus* serine glutamyl endopeptidase, V8 protease and aureolysin.

In certain embodiments the release of biologically active agents from the oligomeric segment can be in response to peptidase enzymes upregulated for certain disease states. For example, a polyamide sequence responsive to cathepsin K can be used where the polymer of the invention is used as part of a treatment for a degenerative bone disease.

The current invention utilizes polyamide linkers that contain cleavage recognition sites for peptidase enzymes. An upregulation of peptidase activity leads to hydrolysis of the polyamide linker and release of the biologically active agent.

Biologically Responsive Polyamide Linkers

Polyamide linkers incorporated in the invention include natural amino acids coupled through amide linkages in linear or branched sequences. The polyamide linkers are designed to be susceptible to hydrolysis by particular endopeptidase enzymes, such as *Staphylococcus aureus* serine glutamyl endopeptidase, V8 protease, metalloproteinases including aureolysin and MMP-9, and exopeptidases such as carboxypeptidase A, carboxypeptidase B, aminopeptidase N/CD, and aminopeptidase P, that are upregulated during a physiological response or pathological process.

Hydrolysis of the polyamide linker occurs at specific protease cleavage recognition sites. In particular, MMP-9 is known to recognize and cleave several consensus sequences; including Pro-X-X-Hy-(Ser/Thr), Gly-Leu-(Lys/Arg), Arg-Arg-X-(Ile/Lys), and Arg-X-(Ile/Lys), where X is any residue and Hy is a hydrophobic residue. MMP-9 has a unique preference for Arg at both $P_2$ and $P_1$ and a preference for Ser/Thr at $P_2$. V8 protease favors glutamic acid and Pro or Leu at the $P_1$ and $P_2$ position, respectively, while the S3 subsite of V8 protease prefers leucine. Aureolysin has a low substrate specificity and cleaves bonds on the N-terminal side of bulky, aliphatic, or hydrophobic residues. Furthermore, human exopeptidases, carboxypeptidase B and aminopeptidases N/CD, target basic residues (Arg/Lys) and Ala, respectively.

To prepare a polymer susceptible to degradation by Cathepsin K, the polyamide linker can include one of the following peptide sequences specifically recognized by this enzyme: KLRFSKQEDD; KXPGSKQEDD; and KPXGSKQEDD (see, for example, Alves et al., *Biochem. J.* 373:981 (2003)).

To prepare a polymer susceptible to degradation in the presence of *Candida albicans*, the polyamide linker can include a peptide sequence recognized by a peptidase enzyme expressed by this organism (e.g., aspartyl proteinases expressed by *C. albicans* recognize the peptide sequence SLASPPTSLVF) (see, for example, Putnam et al., *J. Biol. Chem.* 254:2865 (1979)).

Polymer systems responsive to inflammation can be designed for selective hydrolysis in the presence of enzymes upregulated by inflammatory conditions. Such enzymes and their substrates are listed in Table 1.

TABLE 1

| Peptidase | Alternative Name | Substrate |
|---|---|---|
| MMP-1 | Collagenase; Fibroblast Collagenase; Interstitial Collagenase | Collagens (I, II, III, VII, VIII and X); Gelatin; aggrecan; hyaluronidase-treated versican-C; proteoglycan link protein; large tenascin-C; α1-antitrypsin/α1-proteinase inhibitor ($\alpha_1$-AT); α1-antichymotrypsin ($\alpha_1$-ACHYM); ovostatin; entactin, GST-TNF/TNF peptide; L-Selectin; IL-1β; serum amyloid A; IGF-BP5; IGF-BP3; MMP-2; MMP-9 |
| MMP-2 | 72-kDa Gelatinase; Gelatinase A, Type IV Collagenase; Neutrophil Gelatinase | Collagens (I, IV, V, VII, X, XI and XIV); Gelatin; elastin; fibronectin; laminin-1; laminin-5; galectin-3; aggrecan; decorin; hyaluronidase-treated versican; proteoglycan link protein; osteonectin; MBP; GST-TNF/TNF peptide; IL-1β; prolysyl oxidase fusion protein; IGF-BP5-IGF-BP3; FGF R1; MMP-1; MMP-9; MMP-13 |
| MMP-3 | Stromelysin-1; Transin | Collagen (III, IV, V, IX); Gelatin; aggrecan; perlecan; decorin; proteoglycan link protein; fibronectin; laminin; entactin; osteonectin; elastin; $\alpha_1$-AT; $\alpha_1$-ACHYM |

TABLE 1-continued

| Peptidase | Alternative Name | Substrate |
|---|---|---|
| MMP-7 | Matrilysin, PUMP | Collagen (IV, V, IX); Gelatin; aggrecan; decorin; proteoglycan link protein; fibronectin; laminin; entactin; large and small tenascin-C; osteonectin; b4 intergrin; elastin; casein; transferring; MBP, $\alpha_1$-AT; GST-TNF/TNF peptide; plaminogen; MMP-1; MMP-2; MMP-9 |
| MMP-8 | Neutrophil Collagenase; Collagenase 1 | Collagen (I, II, III, V, VII, VIII and X); Gelatin; aggrecan; $\alpha_1$-AT; $\alpha_1$-ACHYM; $\alpha_2$-antiplasmin; fibronectin |
| MMP-9 | 92 kDa Gelatinase; Gelatinase B | Collagen (IV, V, VII, and X, XIV); Gelatin; elastin; gelectin-3; aggrecan; proteoglycan link protein; fibronectin; entactin; osteonectin; $\alpha_1$-AT; MBP; GST-TNF-TNF peptide, IL-1b; plasminogen |
| MMP-10 | Stromelysin-2 | Collagen (III, IV, V); Gelatin; casein; aggrecan; elastin; proteoglycan link protein; MMP-1, MMP-8 |
| MMP-11 | Stromelysin-3 | A1-Ata2M; casein; IGF-binding protein-1 |
| MMP-12 | Macrophage Metalloelastase | Collagen IV; Gelatin, elastin and κ-elastin; casein; $\alpha_1$-AT; fibronectin; vitronectin; laminin; entactin; proteoglycan monomer; GST-TNF; MBP; fibrinogen; fibrin; plasminogen |
| MMP-13 | Collagenase-3 | Collagen (I, II, and III, IV, IX, X, XIV); Gelatin; $\alpha$1-ACHYM and plasminogen activator inhibitor 2; aggrecan, perlecan; large tenascvin-C and fibronectin; osteonectin; MMP-9 |
| MMP-14 | MT-MMP-1 | Collagen (I, II, III); Gelatin, casein, κ-elastin, fibronectin, laminin, vitronectin and proteoglycans, large tenascin-C, entactin, $\alpha_1$-AT; $\alpha_2$M; GST-TNF, MMP-2, MMP-13 |
| MMP-15 | MT-MMP-2 | Fibronectin, large tenascin-C, entactin, laminin, affrecan, perfexan, GST-TNF, MMP-2 |
| MMP-16 | MT-MMP-3 | Collagen III, Gelatin, casein, fibronectin, MMP-2 |
| MMP-17 | | Gelatin |
| MMP-19 | | Gelatin |
| MMP-20 | Eamelysin | Amelogenin |
| Carboxy-peptidase A | — | Exopeptidase-C-terminal L-amino acid that has an aromatic or branched side chain |
| Carboxy-peptidase B | — | Exopeptidase-basic residues in $P_2$ position (arg/lys) |
| Amino-peptidase N/CD | — | Exopeptidase-affinity for alanine |

Polymer systems responsive to cellular proliferation can be designed for selective hydrolysis in the presence of enzymes upregulated during cell proliferative. Such enzymes and their substrates are listed in Table 2.

TABLE 2

| Peptidase | Substrate |
|---|---|
| Metalloproteases-as listed above (MMP's) | As listed above in Table 1; both endo and exo protease activity |
| MMP-2 | Laminin-5 |
| MMP-3 | E-cadherin |
| MMP-7 | E-cadherin |
| Serine proteases | Fibrinonectin |
| Cysteine proteases | -hydrophobic aliphatic or aromatic residues in the $P_2$ position |
| Chymase | C-terminal proteins after aromatic amino acids (Phe, Tyr, Trp); Ang 1 |

Polymer systems responsive to pain can be designed for selective hydrolysis in the presence of enzymes upregulated in response to pain. Such enzymes and their substrates are listed in Table 3.

TABLE 3

| Peptidase | Substrate |
|---|---|
| Metalloproteases-as listed above (MMP's) | As listed above in Table 1; both endo and exo protease activity |
| Monoamine oxidases (MAO) | |
| Protein Kinase C | Bombesin; Gastrin releasing peptide; gastrin; neuropeptide Y |
| Caspase | Gastrin releasing peptide, gastrin |
| Promycin-sensitive aminopeptidase | Cholecystokinin (CCK); vasopressin, oxytocin |
| Trypsin | Corticotropin; β-lipotropin; Dynorphin; Leumorphin |
| Dynorphin A-17 processing enzyme | Dynorphin |
| Carboxypeptidase A, B | Corticotropin; β-lipotropin; Dynorphin; Endorphin; Enkephaline |
| ATPase | Secretin |
| Aminopeptidase N | Corticotropin; β-lipotropin; Dynorphin; Endorphin; Enkephaline, Secretin, Motilin, Vasoactive intestinal peptide (VIP); Somatostatin; Neurokinin |

TABLE 3-continued

| Peptidase | Substrate |
| --- | --- |
| Proline Endopeptidase | Enkephaline |
| Dipeptidyl peptidase-IV | Glucagon; Growth hormone-releasing factor (GRF) |
| Neprilysin | Tachykinins: Neurokinin A; Neurokinin B; Neuropeptide A; Neuropeptide gamma; Substance P; Tachykinins |
| Andiotensin converting enzyme | Tachykinins: Neurokinin A; Neurokinin B; Neuropeptide A; Neuropeptide gamma; Substance P; Tachykinins |

Polymer systems responsive to muscle spasms can be designed for selective hydrolysis in the presence of enzymes upregulated in response to muscle spasms. Such enzymes and their substrates are listed in Table 4.

TABLE 4

| Peptidase | Substrate |
| --- | --- |
| Metalloproteases-as listed above (MMP's) | As listed above in Table 1; both endo and exo protease activity |

Polyamide linkers may incorporate non-natural or D-amino acids and remain susceptible to hydrolysis by secreted prokaryotic proteases. The V8 protease has a large hydrophobic pocket at its P1' position and can digest a p-nitroanilide substrate. Secreted Prokaryotic proteases may also recognize D-amino acids and preferentially hydrolyze the polyamide linker in the presence of Eukaryotic proteases Polyamide linkers remain stable to exopeptidase activity until hydrolysis by endopeptidases creates polyamide fragments with free carboxy- or amino-termini. The need for aminopeptidases may be minimized by locating endopeptidase cleavage sites at the C-terminus of polyamide linkers attached to the biologically active agent.

Because protease recognition sequences are generally only a few amino acids in length, a relatively short polyamide linker can contain several cleavage recognition sites. Polyamide linkers used in the invention can range from 2 to 60 amino acids in length.

Biologically Active Agents

Biologically active agents that can be incorporated into the invention include therapeutic, diagnostic, and prophylactic agents. They can be naturally occurring compounds, synthetic organic compounds, or inorganic compounds. Agents that can be incorporated into the polymeric compound of the invention include, but are not limited to carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatroban, antibodies, neurotransmitters, psychoactive drugs, oligonucleotides, proteins, lipids, and combinations thereof.

Ideally, the biological agent should have difunctional groups selected from hydroxyl, amine, carboxylic acid or sulfonic acid so that it can be tethered to one or more polyamide linkers. For example, Ciprofloxacin, which contains a free secondary amine and carboxyl groups can be covalently tethered between two polyamide linkers and immobilized.

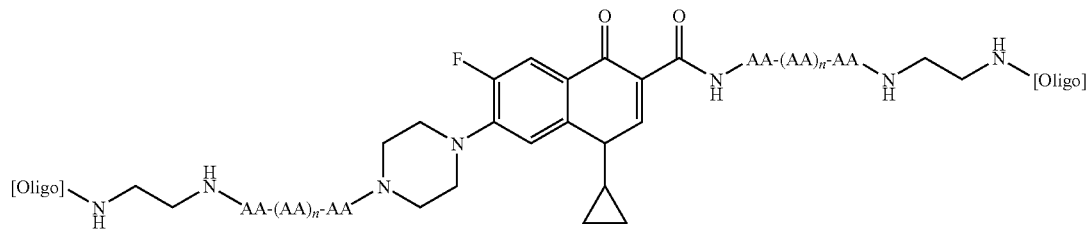

To release higher concentrations of a biologically active agent or a combination of different agents, multiple drugs can be incorporated into the invention through α-substituted glycines in the polyamide linkers. This modification relies on the inherent instability of amino-α-substituted glycines, where the linked α-subunit is a good leaving group (X=—Cl, —Br, —OAc, —SR, or —NR$_2$).

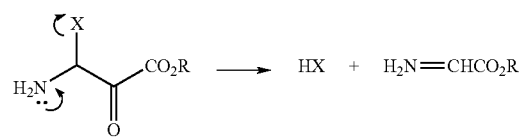

Compounds of this type have been found to rapidly decompose with the expulsion of the α-subunit. The α-substituted glycine remains stable when the amino-terminus is acylated.

The instability of amino-α-substituted glycine provides numerous strategies for incorporating multiple biologically active agents into the invention. Fragmentation of the polyamide linkers by peptidase activity and the collapse of α-substituted glycines lead to the release of larger numbers of biologically active agents.

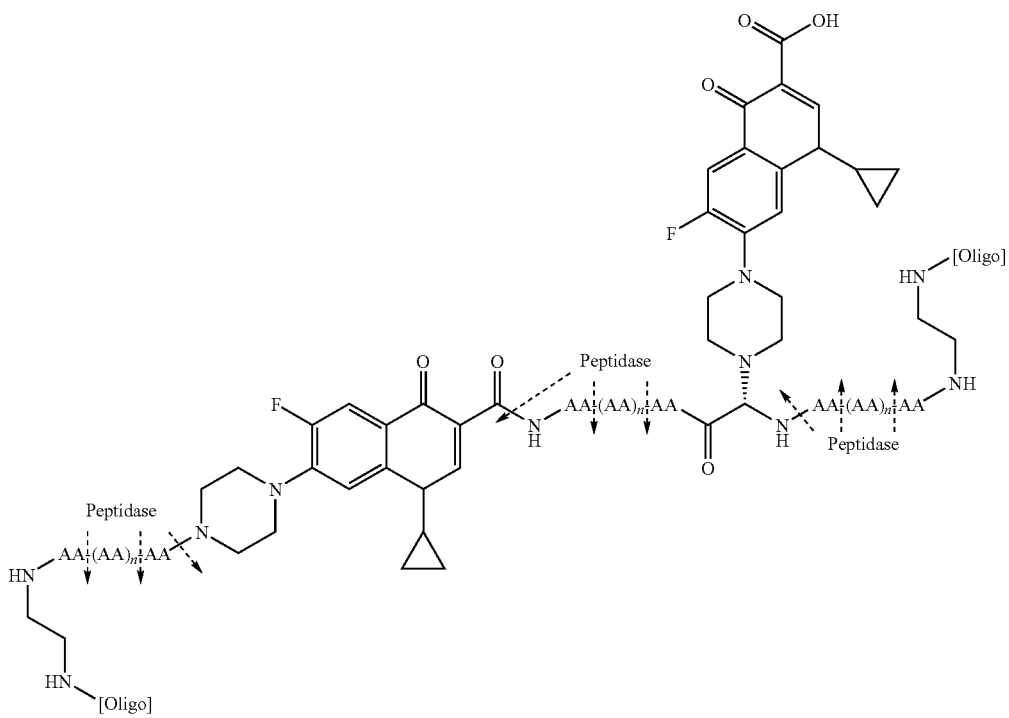

Biological agents can also be linked together through hydrolysable covalent bonds or linking segments. The premature release of drug, caused by hydrolysis of covalent bonds or segments between two drugs, is prevented by the attached oligomeric segment to each drug moiety.

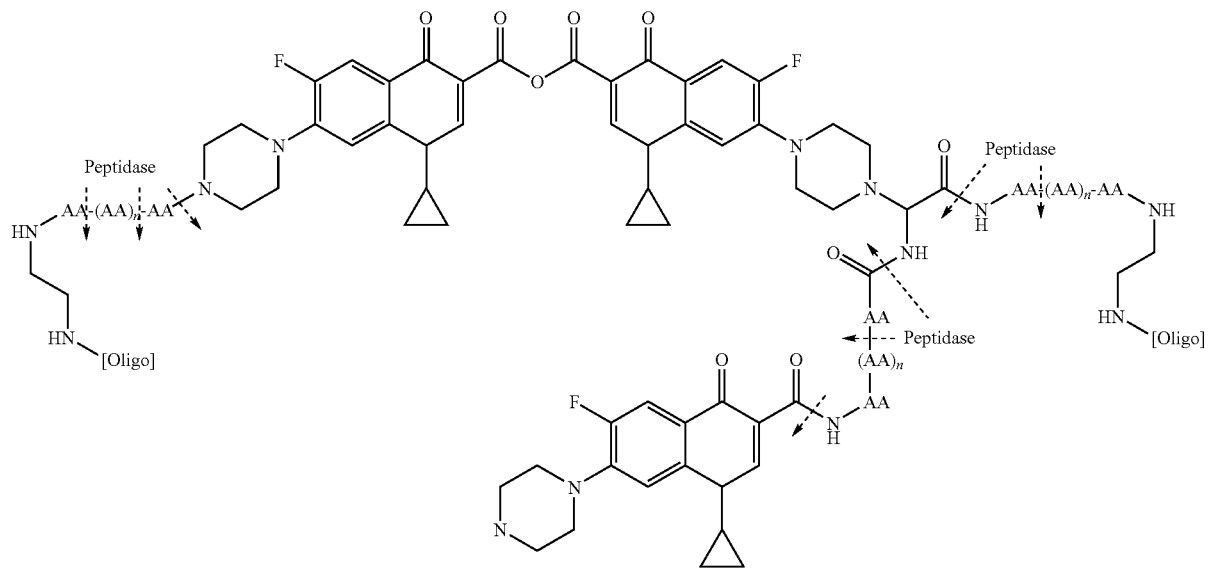

Exemplary therapeutic agents include growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutylric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an anti-inflammatory agent, such as an NSAID, corticosteriod, or COX-2 inhibitor, e.g., rofecoxib, celecoxib, valdecoxib, or lumiracoxib. The therapeutic agent may also include antibiotics.

Exemplary diagnostic agents include imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

Rapamycin Macrolides:

Rapamycin (Sirolimus) is an immunosuppressive lactam macrolide that is produced by *Streptomyces hygroscopicus*. See, for example, McAlpine, J. B., et al., J. Antibiotics 44: 688 (1991); Schreiber, S. L., et al., J. Am. Chem. Soc. 113: 7433 (1991); and U.S. Pat. No. 3,929,992, incorporated herein by reference. Exemplary rapamycin macrolides that can be used in the methods and compositions of the invention include, without limitation, rapamycin, CCI-779, Everolimus (also known as RAD001), and ABT-578 (40-epi-(N1-tetrazolyl)-rapamycin, see, for example, Pagano T. G., *Magn. Reson. Chem.* 43:174 (2005)). CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents:

Exemplary antiproliferative agents which can be used in the methods and compositions of the invention include, without limitation, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids:

Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, predinival, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs:

Exemplary non-steroidal anti-inflammatory drugs (NSAIDs) which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics:

Exemplary analgesics that can be used in the methods and compositions of the invention include, without limitation, fentanyl, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials:

Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinatozole, cefotaxime, ceflizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Local Anesthetics:

Exemplary local anesthetics that can be used in the methods and compositions of the invention include, without limitation, cocaine, procaine, lidocaine, prilocalne, mepivicaine, bupivicaine, articaine, tetracaine, chloroprocaine, etidocaine, and ropavacaine.

Antispasmodic:

Exemplary antispasmodics that can be used in the methods and compositions of the invention include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

Synthesis and Evaluation

The peptides and conjugates which are synthetic intermediates in the synthesis of the polymers of the invention can be readily prepared according to well-established, standard liquid or solid-phase peptide synthesis methods, general descriptions of which are broadly available, or they may be prepared in solution, by the liquid phase method or by any combination of solid-phase, liquid phase and solution chemistry, e.g., by first completing the respective peptide portion and then, if desired and appropriate, after removal of any protecting groups being present. For example, such intermediates can be prepared using conventional solid phase Fmoc or t-Boc chemistry, as described, for example, in Bodanszky, "The Principles of Peptide Synthesis", Hafner, Rees, Trost, Lehn, Schleyer, Zahradnik, Eds., Springer-Verlag, Berlin, 1984, or as described in Scheme 1, below.

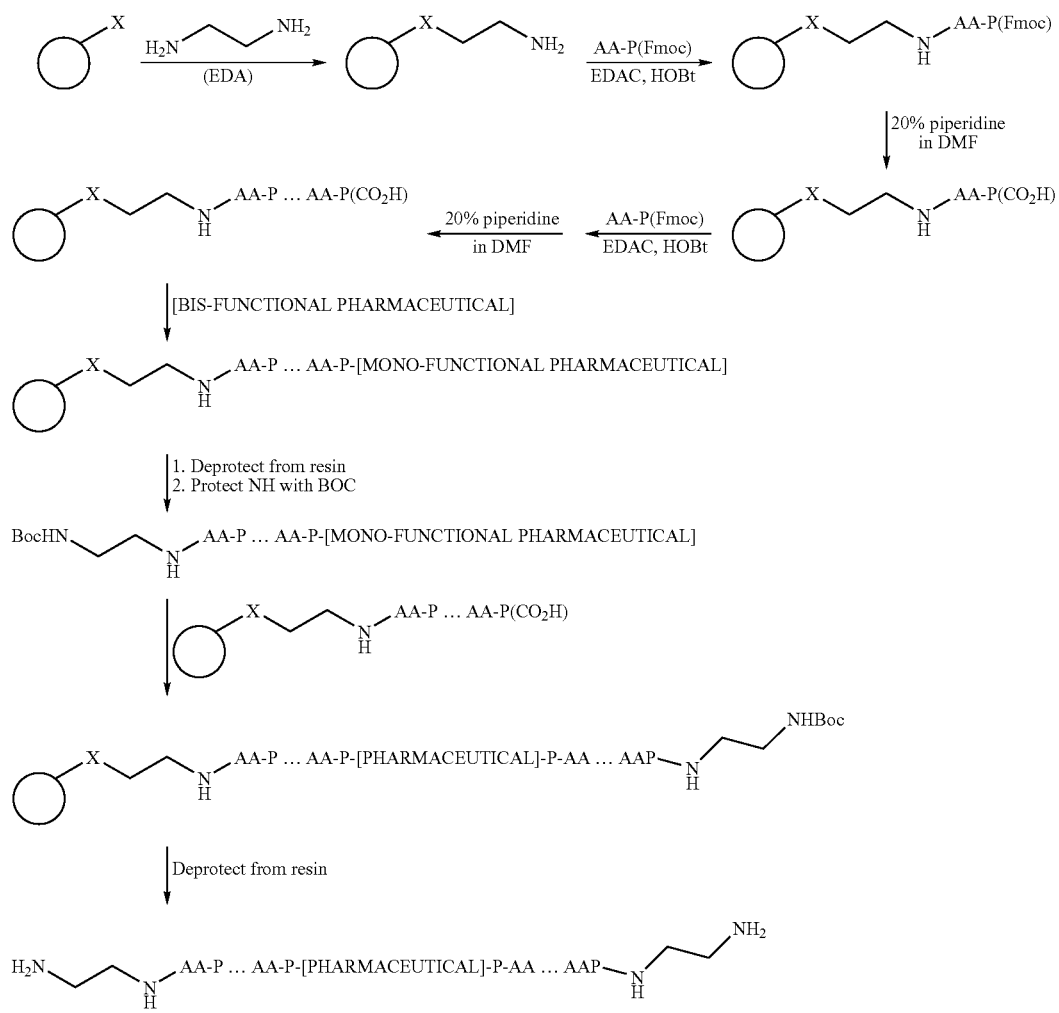

Scheme 1

Using the intermediates described above, the bioresponsive polymers of the invention can be prepared using standard polymer chemistry. For example, urethane based polymers can be prepared as provided in Scheme 2.
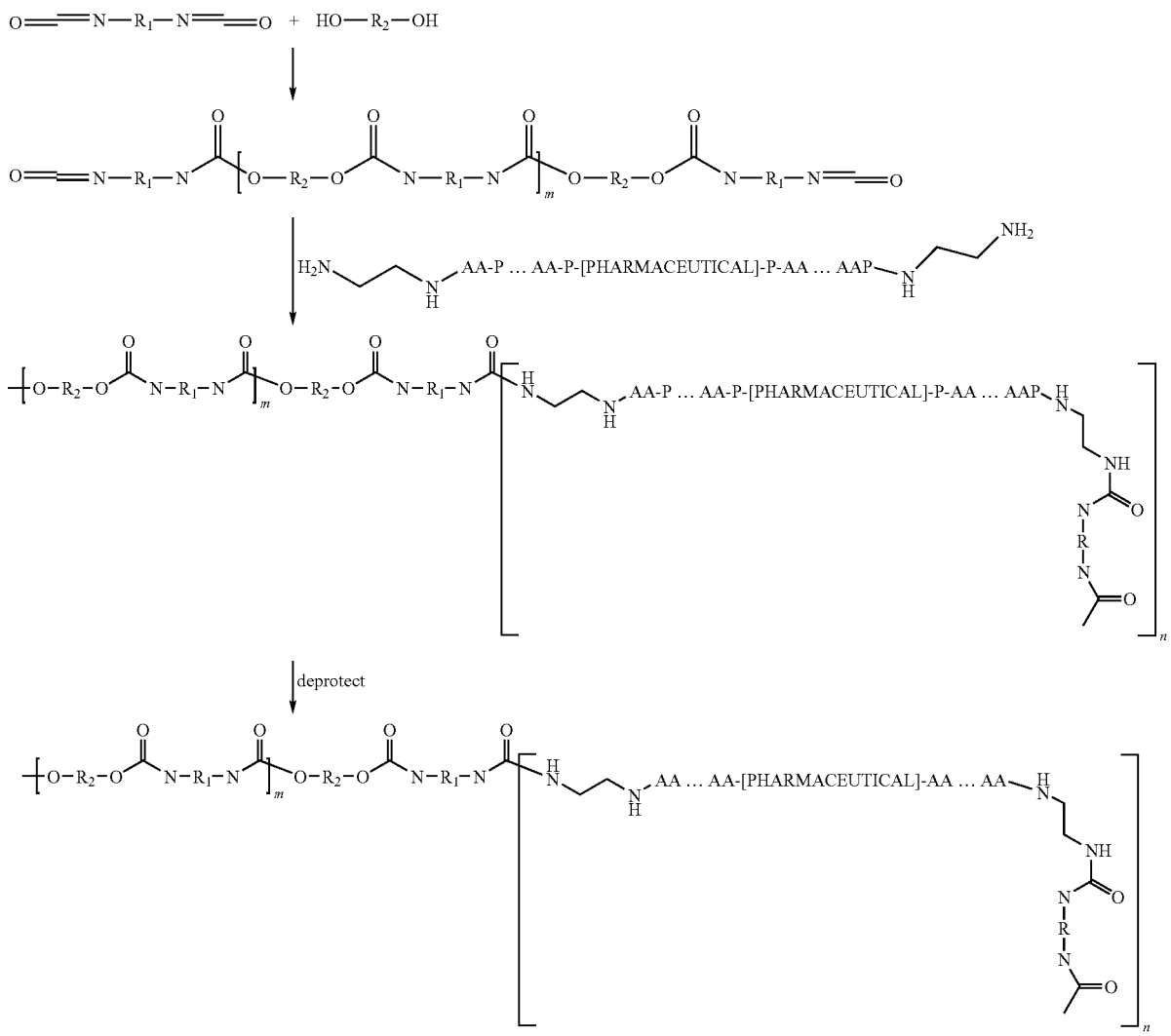
The bioresponsive performance of a polymer of the invention can be tested as provided in Scheme 3, below.
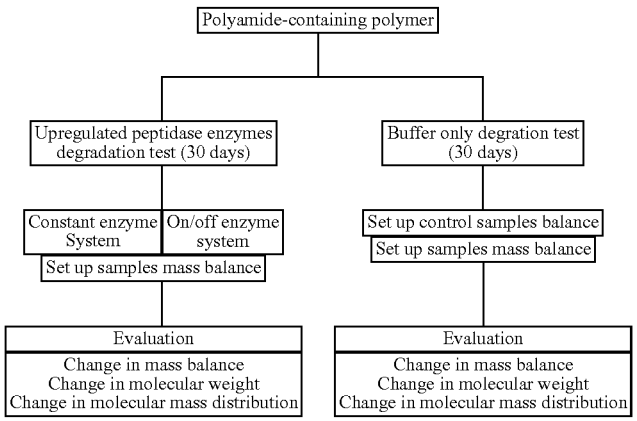

Nondegradable Polymer Systems:

The polymers of the invention can also be configured such that the only degrading portion of the polymer is the peptide specific sequence which is attached to the biologically active agent. These nondegradable polymer systems can be prepared, for example, from poly(butyl methacrylate); acrylonitrile, vinyl acetates and vinyl alcohols. Each of these systems can be adapted to incorporate peptides that are responsive to a particular biological event.

The methacrylate systems can be modified by initial saponification of ester and then the reaction of resulting acid with the amino end of responsive peptide. The acid end can be used to couple a biologically active agent (see Scheme 4).

Scheme 4

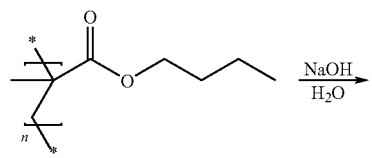

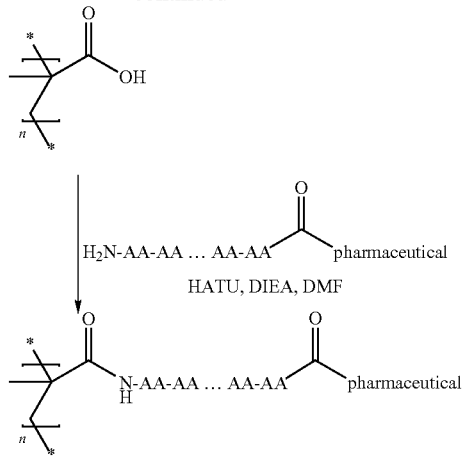

Alternatively, the surface modifying bioactive fluorinated additives described in U.S. Pat. No. 6,770,725 (incorporated herein by reference) can be modified to incorporate peptides that are responsive to a particular biological event. Scheme 5 (below) describes the saponification of the methylester of LDI in these fluorinated additive systems, followed be the amino end attachment to a bioresponsive peptide. The acid end of the peptide is again used for coupling of a biologically active agent.

Scheme 5

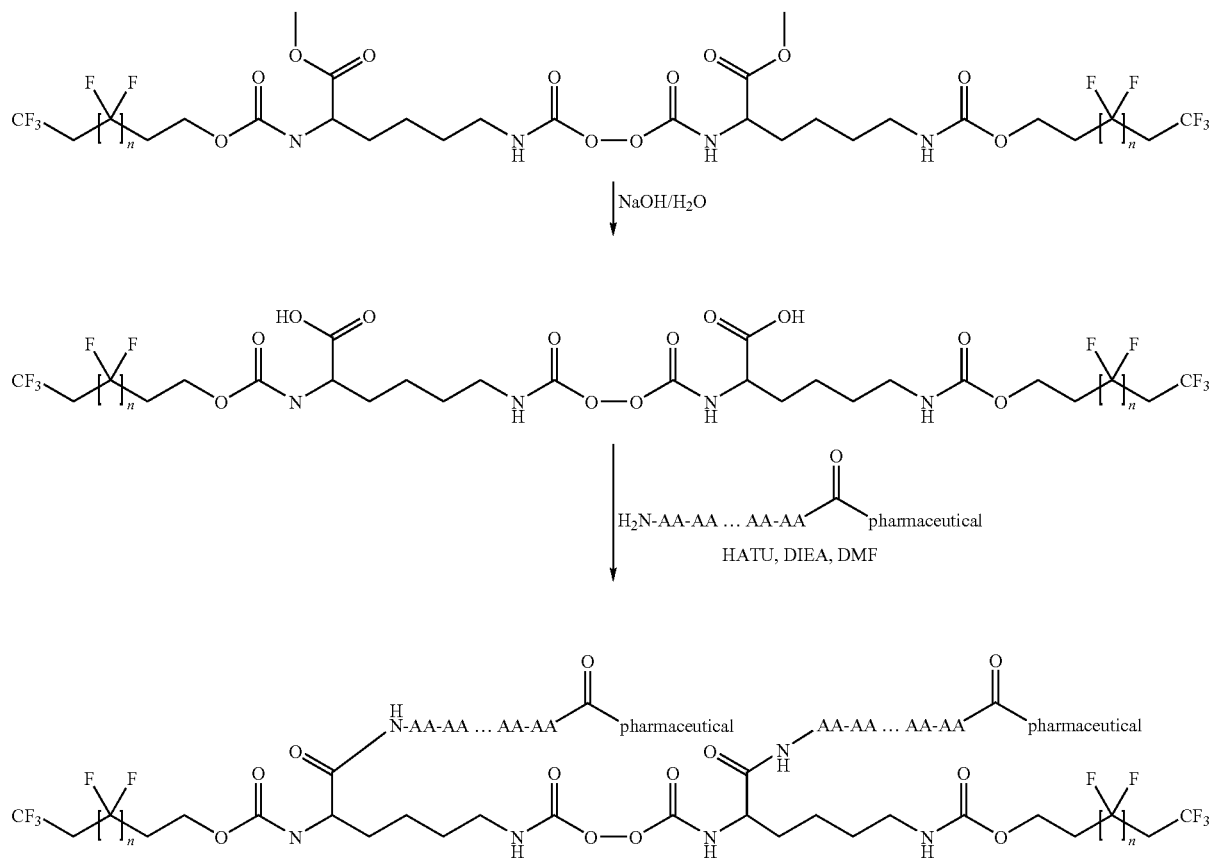

Vinyl acetate systems can be modified by the saponification of the ester to bare an alcohol which can be reacted with the acid end of the bioresponsive peptide followed by reaction of the amino end of the peptide with an appropriate biologically active agent. Alternatively, a more robust linkage can be made by first reacting the alcohol with 2-amino-1-bromoethane followed by the aforementioned reaction with acid portion of the responsive peptide (see Scheme 6).

Scheme 6

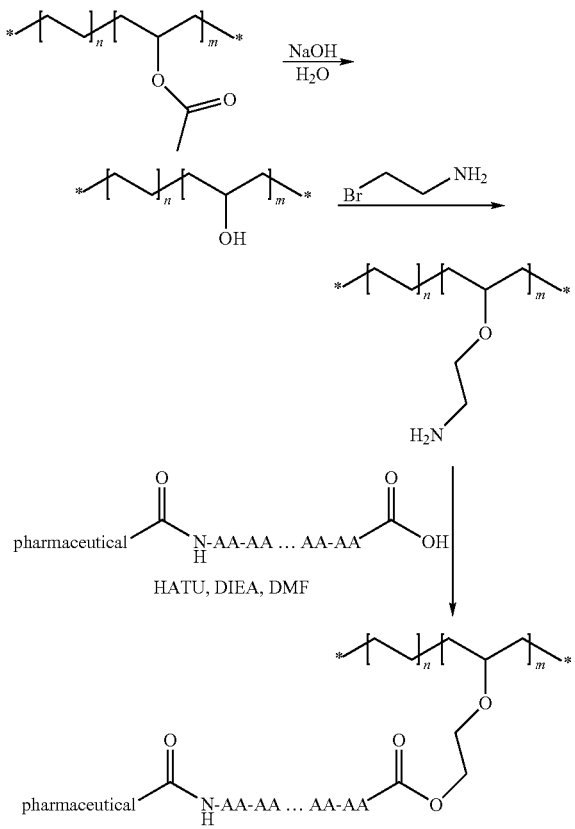

Acrylonitrile polymers can be modified by treatment with acid to transform bared nitrile function to an acid. This acid can be treated in the same manner described in the methacrylate systems to produce a bioresponsive polymer system of the invention (see Scheme 7).

Scheme 7

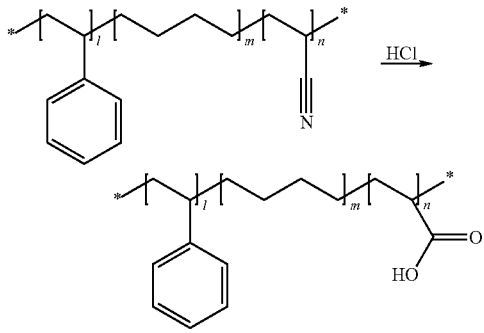

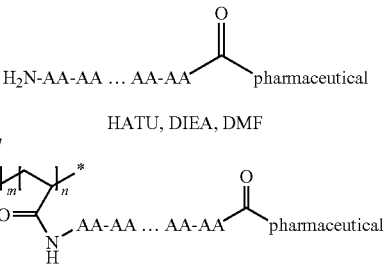

Blends with Base Polymers

Where the polymer of the invention does not have base polymer properties, it may be desirable to prepare a blend with a base polymer to produce the requisite mechanical properties, e.g., for a shaped article. Desirably, the polymer of the invention is concentrated within the nm region of the exterior polymer interface and is designed to be thermodynamically compatible with the base polymer to prevent phase separations.

Many materials having base polymer properties are known in the art. Base polymers useful in the blends of the invention can include, without limitation, polyurethane, polysulfones, polycarbonates, polysaccharides, polyesters, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyethyleneterephthalate, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes.

Shaped Articles

Articles of the invention can be formed from polymer of the invention used either alone or as a blend with a base polymer. One advantage of using a polymer of the invention alone as the base polymer to form a shaped article is that because there is no polymer mixing, there is no reduction in entropy and no possibility of phase separation.

Any shaped article can be made using the compositions of the invention. For example, articles suitable for contact with bodily fluids, such as medical devices can be made using the compositions described herein. The duration of contact may be short, for example, as with surgical instruments or long term use articles such as implants. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

An implantable medical device as described above is generally structured from a base metallic or polymeric platform in a solid state format. The polymer of the invention within this primary platform, either alone or as a blend, controls the release of therapeutic agents from the device.

The methods and compositions of the invention can also be used to deliver a biologically active agent to the surface of a cosmoceutical (e.g., creams, gels, and lotions), to a pellet, e.g., for controlling the proliferation of pests, such as weeds or insects, or to a membrane, for example, for use in a water purification process in which an antibacterial agent is released into the water.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

ABBREVIATIONS

Boc: t-Butyloxycarbonyl
Fmoc: 9-Fluorenylmethyl
DMF: Dimethylformamide
DIEA: Diisoproylethyl amine
HATU: O-(7-Azabenzotriazol-1-yl)-N,N,N',N'-tetramethyluronium PF6
MALDI: Matrix Assisted Laser Desorption Ionization
MS: Mass Spectometer
MMP: Matrix Metalloproteinase
SAP: Aspartic Proteinases
SEC: Trimethyl silyl ethoxy carbonyl
THF: Tetrahydrofuran
TFA: Trifluoroacetic acid
TOF: Time of Flight

TABLE 4

Exemplary Peptides

| Peptide I.D. | M.W. | Disease State (Up-regulated Protease Targeted) | Peptide |
|---|---|---|---|
| LAR-6139(A) | 2143.10 | Inflammation (MMP-9) | Protected: β-Ala-gly-ser-gly-arg-pro-arg-gln-ile-thr-ala-ala (SEQ ID NO. 3) |
| LAR-6139 | 1184.65 | Inflammation (MMP-9) | β-Ala-gly-ser-gly-arg-pro-arg-gln-ile-thr ala-ala (SEQ ID NO. 4) |
| LAR-7009(A) | 3065.5 | Inflammation (MMP-9) | Protected: Pro-arg-arg-arg-arg-pro-arg-gln-ile-thr-ala (SEQ ID NO. 5) |
| LAR-7009 | 1406.85 | Inflammation (MMP-9) | Pro-arg-arg-ard-arg-pro-arg-gln-ile-thr-ala (SEQ ID NO. 6) |
| LAR-7022(A) | 2064.18 | Microbial Excreted Proteases (aureolysin, staphopain) | Protected: β-ala-asp-asp-ile-gly-thr-ser-arg-pro-gln-glu (SEQ ID NO. 7) |
| LAR-7022 | 1188.5 | Microbial Excreted Proteases (aureolysin, staphopain) | β-ala-asp-asp-ile-gly-thr-ser-arg-pro-gln-glu (SEQ ID NO. 8) |
| LAR-7023(A) | 1810.18 | Microbial Excreted Proteases (aureolysin, staphopain) | Protected: Phe-ala-ala-gly-ile-gly-thr-ser-arg-pro-gln (SEQ ID NO. 9) |
| LAR-7023 | 1104.58 | Microbial Excreted Proteases | Phe-ala-ala-gly-ile-gly-thr-ser-arg-pro-gln (SEQ ID NO. 10) |
| LAR-7024(A) | 886.0 | Microbial Excreted Proteases (aureolysin, staphopain) | Protected: Gly-gly-gly-gly-gly-ala-leu-leu-glu (SEQ ID NO. 11) |
| LAR-7024 | 730.37 | Microbial Excreted Proteases (V8 protease) | Gly-gly-gly-gly-gly-ala-leu-leu-glu (SEQ ID NO. 12) |
| LAR-7041(A) | 1571.82 | Fungal Excreted Proteases (SAP) | Protected: β-ala-gly-lys-pro-ala-leu-phe-phe-arg-leu (SEQ ID NO. 13) |
| LAR-7041 | 1119.67 | Fungal Excreted Proteases (SAP) | β-ala-gly-lys-pro-ala-leu-phe-phe-arg-leu |
| LAR-7042(A) | 1514.00 | Fungal Excreted Proteases (SAP) | Protected: β-ala-ser-leu-ala-ser-pro-pro-thr-ser-leu-val-phe (SEQ ID NO. 14) |

TABLE 4-continued

Exemplary Peptides

| Peptide I.D. | M.W. | Disease State (Up-regulated Protease Targeted) | Peptide |
| --- | --- | --- | --- |
| LAR-7042 | 1189.65 | Fungal Excreted Proteases (SAP) | β-ala-ser-leu-ala-ser-pro-pro-thr-ser-leu-val-phe (SEQ ID NO. 15) |
| LAR-7043(A) | 1051.14 | Fungal Excreted Proteases (SAP) | Protected: Gly-lys-pro-ala-leu-phe-phe-ala leu (SEQ ID NO. 16) |
| LAR-7043 | 963.57 | Fungal Excreted Proteases (SAP) | Gly-lys-pro-ala-leu-phe-phe-ala-leu (SEQ ID NO. 17) |
| LAR-7044(A) | 2339.74 | Fungal Excreted Proteases (SAP) | Protected: β-ala-lys-leu-arg-phe-ser-lys-gln-glu-asp-asp (SEQ ID NO. 18) |
| LAR-7044 | 1336.45 | Fungal Excreted Proteases (SAP) | β-ala-lys-leu-arg-phe-ser-lys-gln-glu-asp-asp (SEQ ID NO. 19) |
| LAR-7047 | 1024.18 | — | Control 1: val-phe-phe-arg-arg-gln-thr-ala (SEQ ID NO. 1) |
| LAR-7048 | 742.93 | — | Control 2: pro-arg-arg-ile-sys-val (SEQ ID NO. 2) |

Synthesis:

Materials:

The protected amino acids, NovaSyn® TGT resins where obtained from Novabiochem, San Diego Calif. and used as received. Anhydrous dimethylformamide, O-(7-Azabenzotriazol-1-yl)-N,N,N',N'-tetramethyluronium PF6 (HATU), diisoproylethyl amine (DIPEA), 9-Fluorenylmethyl N-(2-aminoethyl)carbamate hydrobromide, zinc bromide, anhydrous methylenechloride, chloroform, methanol, acetic acid, N-(3-dimethylaminopropyl)-N'-ethylcarbodiimide hydrochloride, ciprofloxacin, TFA, piperidine was obtained from Sigma Chemical Co., St. Louis Mo. and used without further purification. Matrix Metalloproteinase-9 was obtained from Chemicon, Temecula, Calif. Staphopain A and Staphopain B were obtained from BioCentrum, Kraków Poland. Aureolysin was obtained from Axxora, San Diego, Calif. $V_8$ Proteinase was obtained from Mo Bi Tec, Marco Island, Fla. SAP was obtained from TaKaRa, Otsu, Japan. Carboxypeptidase, Aminopeptidase P was obtained from Sigma St. Louis Mo.

Example 1

Preparation of 2-(trimethylsilyl)ethyl-4-nitrophenyl Carbonate (1)

To a dry 100 mL two necked round bottom flask equipped with a condenser and a dropping funnel flushed with nitrogen was added 4-nitrophenyl chloroformate (6.88 g, 34 mmol) and DCM (50 mL). To this stirring solution via the dropping funnel 2-(trimethylsilyl)ethanol (4.0 g, 34 mmol) in pyridine (3 mL) and DCM (3 mL) was added dropwise over 30 minutes. Heat was generated and the clear solution became slightly cloudy. After returning to room temperature, the solution was allowed to stand for 2 h. Extraction with 0.5 M HCl (150 mL), washing of the organic later to neutrality, drying with sodium sulfate, filtering, and evaporation under reduced pressure gave a light yellow oil. Filtration of the triturated 4-nitrophenyl carbonate 1 with hexane (185 mL), followed by removal of solvent under reduced pressure produced an oil, which was stirred with ice-cold water (150 mL) containing a drop of 2 N formic acid. The white precipitate that formed was filtered and dried overnight at room temperature under reduced pressure: yield 8.3 g (87%); $R_f$=0.93 in 10% methanol in chloroform; mp 35-36° C. [lit. mp 34.3-35.9° C.]

Example 2

Preparation of N-(2-trimethylsilyl)ethyl-4-nitrophenyl Carbonyl) Ciprofloxacin (2)

To a dry 100 mL round bottom flask was added ciprofloxacin hydrochloride (1.66 g, 5.0 mmol), sodium carbonate (2.65 g, 25 mmol) in water (12.5 mL) and THF (12.5 mL). To this resulting solution was added 1 (1.45 g, 5.12 mmol). The reaction mixture was stirred at room temperature for 30 h. To the resulting yellow solution was added sodium thiosulphate (3.625 g, 20 mmol) to bleach the tallow color (reduction of p-nitrophenol to p-aminophenol). The resulting solution was adjusted to a pH of 6.0 with the addition of 1.0 N HCl. The system was transferred to a separatory funnel where it was extracted with chloroform (3×100 mL). The combined organic layer was dried over sodium sulphate, filtered, and removed under reduced atmosphere. This produced 2.33 g of crude product which was purified using column chromatography eluting with 1.5% methanol in chloroform. This produced 1.353 g (57%) of the desired product ($R_f$=0.60 in 10% methanol in chloroform). $^1$H NMR of 2: (400 MHz, CDCl$_3$). δ: 8.73 (s, 1H, OH), 8.00 (s, 2H, ar-H and vinyl-H), 7.40 (d, 1H, J=9.4 Hz, ar-H), 4.17 (t, 2H, J=12.16 Hz, SiCH$_2$CH$_2$O), 3.69 (q, 4H, J=6.8 Hz, N—CH$_2$CH$_2$NCO), 3.25 (q, 4H, J=4.8 Hz, N—CH$_2$—CH$_2$NCO) 1.34 (q, 2H, J=8.64, cyclopropyl-H), 1.19 (t, 1H, J=8.64, cyclopropyl-H), 1.14 (m, 62H, cyclopropyl-H), 0.97 (t, 2H, J=12.16 Hz, SiCH$_2$CH$_2$O), 0.00 (s, 9H, Si(CH$_3$)$_3$). EI-MS of 2 (m/z, %): Calculated for mass C$_{23}$H$_{30}$FN$_3$O$_5$Si: 475.58 amu. found 475.31 (M$^+$, 30); 432.2 (20), 231.2 (65). See Scheme 8 below.

Scheme 8 Preparation of SEC protection of Ciprofloxacin

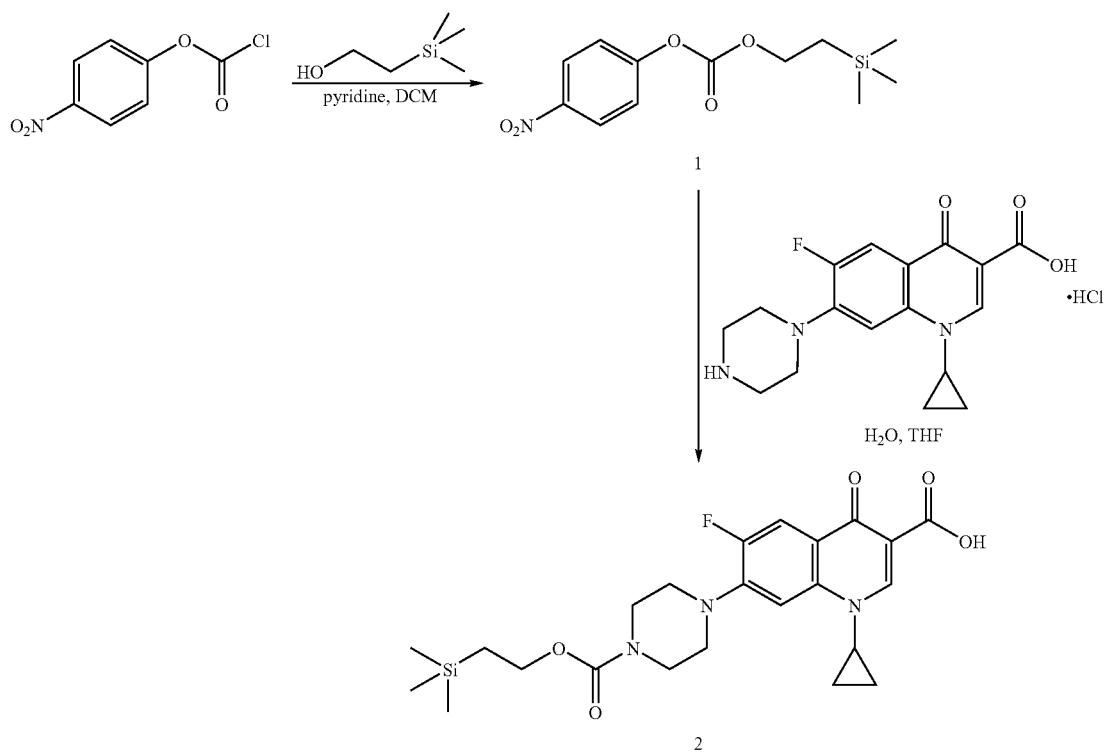

Example 3

Preparation of LAR-6139

Peptide synthesis was conducted with a NovaSyn Crystal Automated Peptide Synthesizer (1990) using Fmoc chemistry. A typical coupling process was conducted with NovaBiochem TGT resin. The initial purchased Fmoc protected amino acid resin was deprotected by the treatment with 20% piperidine in DMF solution for 10 minutes. The resin was washed with DMF (2×20 mL) after each coupling and Fmoc deprotection step. Coupling was performed with 4M of fmoc protected amino acid activated with 4M HATU and 8M diisopropylethyl amine in DMF (4.5 mL) for 5 minutes before addition into the reaction chamber containing 1M of resin. The coupling is allowed to proceed for 1 h at ambient temperature before the process of deprotection and coupling is repeated. The last amino acid was a Boc protected amino acid to afford the corresponding peptide with Boc amino acid at the N-terminal end. The protected peptide was cleaved from resin using 0.5% TFA in DCM for 1 h followed by neutralization with DIPEA ($R_f$=0.23 in 10% methanol, 0.5% Acetic acid in Chloroform). The free peptide was produced by treatment with neat TFA. Removal of the solvent followed by lyothilization provided the desired product. MALDI-TOF MS: Calculated for $C_{48}H_{85}N_{19}O_{16}$ (β-Ala-gly-ser-gly-arg-pro-arg-gln-ile-thr-ala-ala): 1184.31 amu. found 1184.65.

Example 4

Preparation of LAR-7009

The compound was prepared in the same manner as EXAMPLE 3 starting with fmoc alanine NovaBiochem TGT resin. This produced the desired compound as a white solid after lyophylization. The protected peptide was cleaved from resin using 0.5% TFA in DCM for 1 h followed by neutralization with DIPEA ($R_f$=0.38 in 10% methanol, 0.5% Acetic acid in Chloroform). The free peptide was produced by treatment with neat TFA. Removal of the solvent followed by lyothilization provided the desired product. MALDI-TOF MS: Calculated for $C_{58}H_{107}N_{27}O_{14}$ (Pro-arg-arg-arg-arg-pro-arg-gln-ile-thr-ala): 1406.64 amu. found 1406.85.

Example 5

Preparation of LAR-7022

The compound was prepared in the same manner as EXAMPLE 3 starting with fmoc glutamic acid NovaBiochem TGT resin. This produced the desired compound as a white solid after lyophylization. The protected peptide was cleaved from resin using 0.5% TFA in DCM for 1 h followed by neutralization with DIPEA ($R_f$=0.26 in 10% methanol, 0.5% Acetic acid in Chloroform). The free peptide was produced by treatment with neat TFA. Removal of the solvent followed by lyothilization provided the desired product.

MALDI-TOF MS: Calculated for $C_{47}H_{77}N_{15}O_{21}$ (Pro-arg-arg-arg-arg-pro-arg-gln-ile-thr-ala): 1406.64 amu. found 1188.5.

Example 6

Preparation of LAR-7023

The compound was prepared in the same manner as EXAMPLE 3 starting with fmoc glutamine NovaBiochem TGT resin. This produced the desired compound as a white solid after lyophylization. The protected peptide was cleaved from resin using 0.5% TFA in DCM for 1 h followed by neutralization with DIPEA ($R_f$=0.26 in 10% methanol, 0.5% Acetic acid in Chloroform). The free peptide was produced by treatment with neat TFA. Removal of the solvent followed by lyothilization provided the desired product. MALDI-TOF MS: Calculated for $C_{47}H_{77}N_{15}O_{21}$ (Phe-ala-ala-gly-ile-gly-thr-ser-arg-pro-gln): 1104.22 amu. found 1104.58.

Example 7

Preparation of LAR-7024

The compound was prepared in the same manner as EXAMPLE 3 starting with fmoc glutamic acid NovaBiochem TGT resin. This produced the desired compound as a white solid after lyophylization. The protected peptide was cleaved from resin using 0.5% TFA in DCM for 1 h followed by neutralization with DIPEA ($R_f$=0.21 in 10% methanol, 0.5% Acetic acid in Chloroform). The free peptide was produced by treatment with neat TFA. Removal of the solvent followed by lyothilization provided the desired product. MALDI-TOF MS: Calculated for $C_{30}H_{51}N_9O_{12}$ (Gly-gly-gly-gly-gly-ala-leu-leu-glu): 730.00 amu. found 730.37.

Example 8

Preparation of LAR-7041

The compound was prepared in the same manner as EXAMPLE 3 starting with fmoc leucine acid NovaBiochem TGT resin. This produced the desired compound as a white solid after lyophylization. The protected peptide was cleaved from resin using 0.5% TFA in DCM for 1 h followed by neutralization with DIPEA ($R_f$=0.16 in 10% methanol, 0.5% Acetic acid in Chloroform). The free peptide was produced by treatment with neat TFA. Removal of the solvent followed by lyothilization provided the desired product. MALDI-TOF MS: Calculated for $C_{55}H_{86}N_{14}O_{11}$ (β-ala-gly-lys-pro-ala-leu-phe-phe-arg-leu): 1119.36 amu. found 1119.67.

Example 9

Preparation of LAR-7042

The compound was prepared in the same manner as EXAMPLE 3 starting with fmoc phenylalanine NovaBiochem TGT resin. This produced the desired compound as a white solid after lyophylization. The protected peptide was cleaved from resin using 0.5% TFA in DCM for 1 h followed by neutralization with DIPEA ($R_f$=0.13 in 10% methanol, 0.5% Acetic acid in Chloroform). The free peptide was produced by treatment with neat TFA. Removal of the solvent followed by lyothilization provided the desired product. MALDI-TOF MS: Calculated for $C_{55}H_{88}N_{12}O_7$ (β-ala-ser-leu-ala-ser-pro-pro-thr-ser-leu-val-phe): 1189.36 amu. found 1189.65.

Example 10

Preparation of LAR-7043

The compound was prepared in the same manner as EXAMPLE 3 starting with fmoc phenylalanine NovaBiochem TGT resin. This produced the desired compound as a white solid after lyophylization. The protected peptide was cleaved from resin using 0.5% TFA in DCM for 1 h followed by neutralization with DIPEA ($R_f$=0.27 in 10% methanol, 0.5% Acetic acid in Chloroform). The free peptide was produced by treatment with neat TFA. Removal of the solvent followed by lyothilization provided the desired product. MALDI-TOF MS: Calculated for $C_{49}H_{74}N_{10}O_{10}$ (Gly-lys-pro-ala-leu-phe-phe-ala-leu): 963.17 amu. found 963.57.

Example 11

Preparation of LAR-7044

The compound was prepared in the same manner as EXAMPLE 3 starting with fmoc aspartic acid NovaBiochem TGT resin. This produced the desired compound as a white solid after lyophylization. The protected peptide was cleaved from resin using 0.5% TFA in DCM for 1 h followed by neutralization with DIPEA ($R_f$=0.18 in 10% methanol, 0.5% Acetic acid in Chloroform). The free peptide was produced by treatment with neat TFA. Removal of the solvent followed by lyothilization provided the desired product. MALDI-TOF MS: Calculated for $C_{57}H_{93}N_{17}O_{20}$ (β-ala-lys-leu-arg-phe-ser-lys-gln-glu-asp-asp): 1336.45 amu. found 1336.70.

Example 12

Preparation of LAR-7047

The compound was prepared in the same manner as EXAMPLE 3 starting with fmoc alanine NovaBiochem TGT resin. This produced the desired compound as a white solid after lyophylization. The free peptide was produced by treatment with neat TFA. Removal of the solvent followed by lyothilization provided the desired product. MALDI-TOF MS: Calculated for $C_{49}H_{74}N_{10}O_{10}$ (val-phe-phe-arg-arg-gln-thr-ala): 1024.17 amu. found 1024.55.

Example 13

Preparation of LAR-7048

The compound was prepared in the same manner as EXAMPLE 3 starting with fmoc alanine NovaBiochem TGT resin. This produced the desired compound as a white solid after lyophylization. The free peptide was produced by treatment with neat TFA. Removal of the solvent followed by lyothilization provided the desired product. MALDI-TOF MS: Calculated for $C_{31}H_{58}N_{12}O_7S$ (Pro-arg-arg-ile-sys-val): 742.93 amu. found 743.45.

Example 14

Preparation of LAR-6139-CIPRO-LAR-7009

In step A, peptide LAR-7009 (A) (200 mg, 0.065 mmol) was reacted with ethylene fmoc ethylene diamine (23.7 mg, 0.065 mmol) and DIEA (25 μL, 0.14 mmol) overnight. After reaction was finished, DMF was removed by rotary evaporator. The residue was dissolved in DCM and transferred to separatory funnel were washed with brine (2×20 mL). The combined aqueous layer was back extracted with DCM (1×20 mL). The combined organic layer was dried over sodium sulphate, filtered, and removed under reduced atmosphere. This produced 107 mg (50%) of a crude mixture which was used in the next synthetic step without further purification ($R_f$=0.37 in 10% methanol, 0.5% Acetic acid in Chloroform). The material thus obtained was dissolved in DCM (5 mL) and to this stirring solution was zinc bromide (3.6 g, 15.91 mmol). The resulting heterogeneous mixture was stirred at ambient temperature for 24 h. The system was diluted with DCM (30 mL) and transferred to a separatory funnel where it was washed with brine (2×20 mL). The aqueous layer was back extracted with DCM (11×10 mL). The combined organic layer was dried over sodium sulphate, filtered, and removed under reduced atmosphere. Product 3 was isolated by column chromatograph using the developer of chloroform/methanol/acetic acid solution (9:1:0.5). This produced 45 mg (50%) of the desired product ($R_f$=0.14 in 10% methanol, 0.5% Acetic acid in Chloroform).

In step B, SEC protected ciprofloxacin (2) (6.7 mg, 0.013 mmol) was activated with HATU (5.8 mg, 0.015 mmol) in DMF (2 mL) and DIEA (5.3 μL, 0.03 mmol). After 5 minutes activation time 3 (45 mg, 0.013 mmol) in DMF (1 mL) was added and the resulting solution was allowed to stir overnight. After reaction was finished, DMF was removed by rotary evaporator. The residue was dissolved in DCM (100 mL) and transferred to separatory funnel were washed with brine (2×20 mL). The combined aqueous layer was back extracted with DCM (1×20 mL). The combined organic layer was dried over sodium sulphate, filtered, and removed under reduced atmosphere. Product 4 was isolated by column chromatograph using the developer of chloroform/methanol/acetic acid solution (9:1:0.5). This produced 45 mg (50%) of the desired product ($R_f$=0.33 in 10% methanol, 0.5% Acetic acid in Chloroform).

In step C, process 1, 2 (43 mg, 0.017 mmol) was dissolved in THF (3 mL) in a 10 mL reaction vessel. To this stirring solution was added TBAF (1M, 2 mL, 2 mmol). The solution was allowed to stir at 38° C. for 2 hours, upon which time the solvent was removed under reduced atmosphere. The residue was dissolved in DCM (100 mL) and transferred to a separatory funnel, where it was washed with water (2×10 mL). The combined organic layer was dried over sodium sulphate, filtered, and removed under reduced atmosphere. This produced 9.0 mg of the crude product which was used in the subsequent coupling with no further purification ($R_f$=0.60 in 10% methanol, 0.5% Acetic acid in Chloroform).

In process 2, LAR-6139 (A) (8 mg, 0.0036 mmol) was coupled to the product produced in process 1 (9 mg, 0.0036 mmol) via pre-activation of former material with HATU (1.5 mg, 0.004 mmol) in DMF (1 mL) and DIEA (1.4 μL, 0.008 mmol) in the same manner described above. Product from process 1 was dissolved in 1 mL of DMF before addition into the coupling reaction. After reaction was finished, DMF was removed by rotary evaporator. The residue was dissolved in DCM (100 mL) and transferred to separatory funnel were washed with brine (2×20 mL). The combined aqueous layer was back extracted with DCM (1×20 mL). The combined organic layer was dried over sodium sulphate, filtered, and removed under reduced atmosphere. Product thus produced was treated with 90% TFA in DCM (2 ml) for 1 hour at room temperature. The solution was neutralized with the addition of piperidine. Upon completion the solvent was removed under reduced atmosphere. The resulting residue was treated with 20% piperidine in DMF for 20 minutes. Product 5 was isolated by column chromatograph using the developer of chloroform/methanol/acetic acid solution (8:2:1.0). This produced 10 mg (63%) of the desired product ($R_f$=0.15 in 20% methanol, 1.0% Acetic acid in Chloroform). MALDI-TOF MS: Calculated for $C_{115}H_{184}FN_{39}O_{31}$: 2627.93 amu. found 2627.95. See Scheme 9 below.

Scheme 9
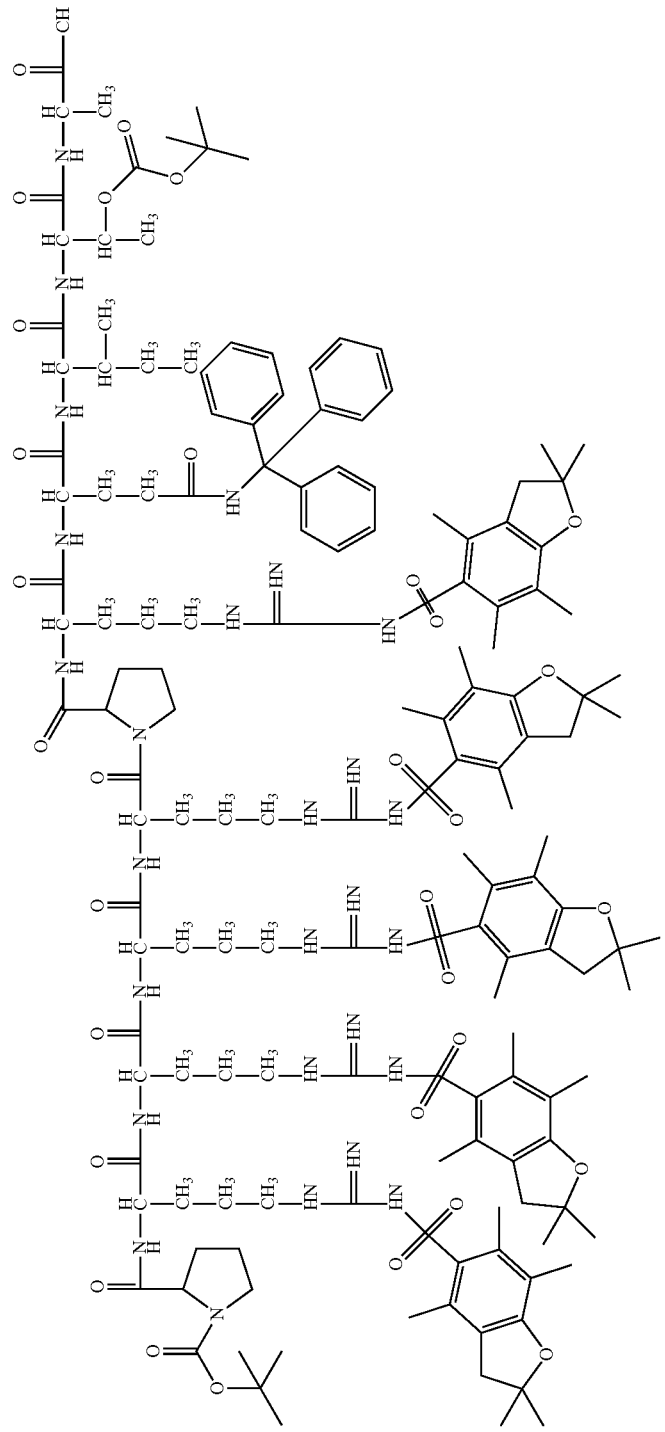
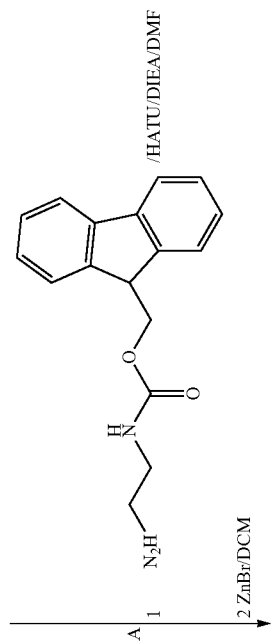

-continued
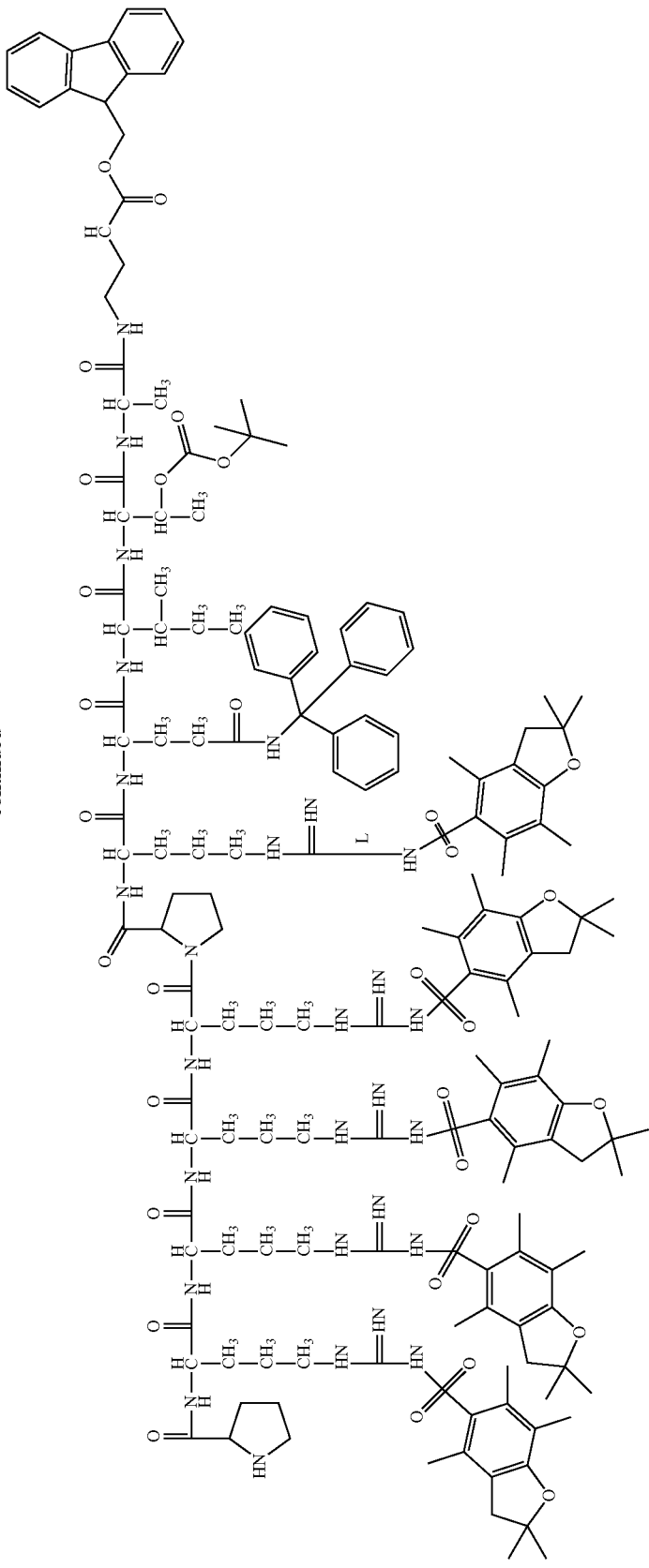
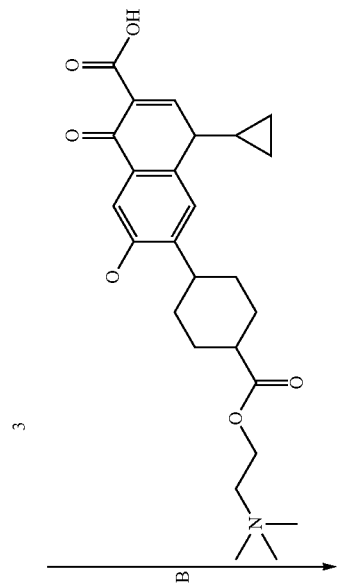

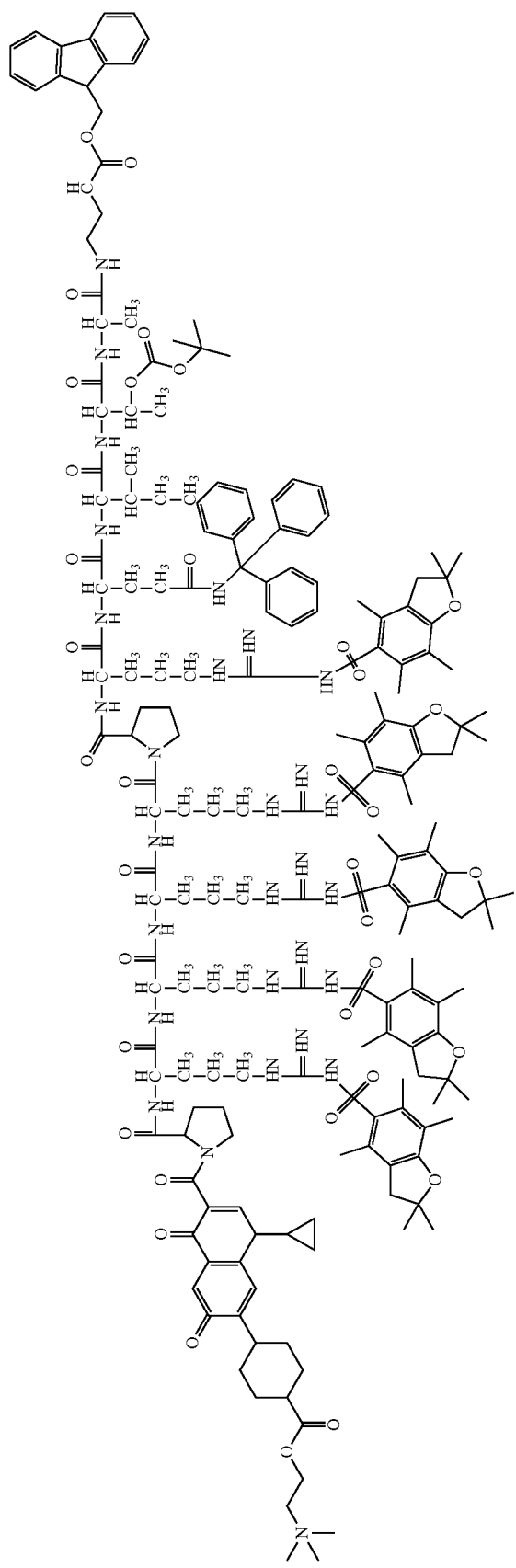

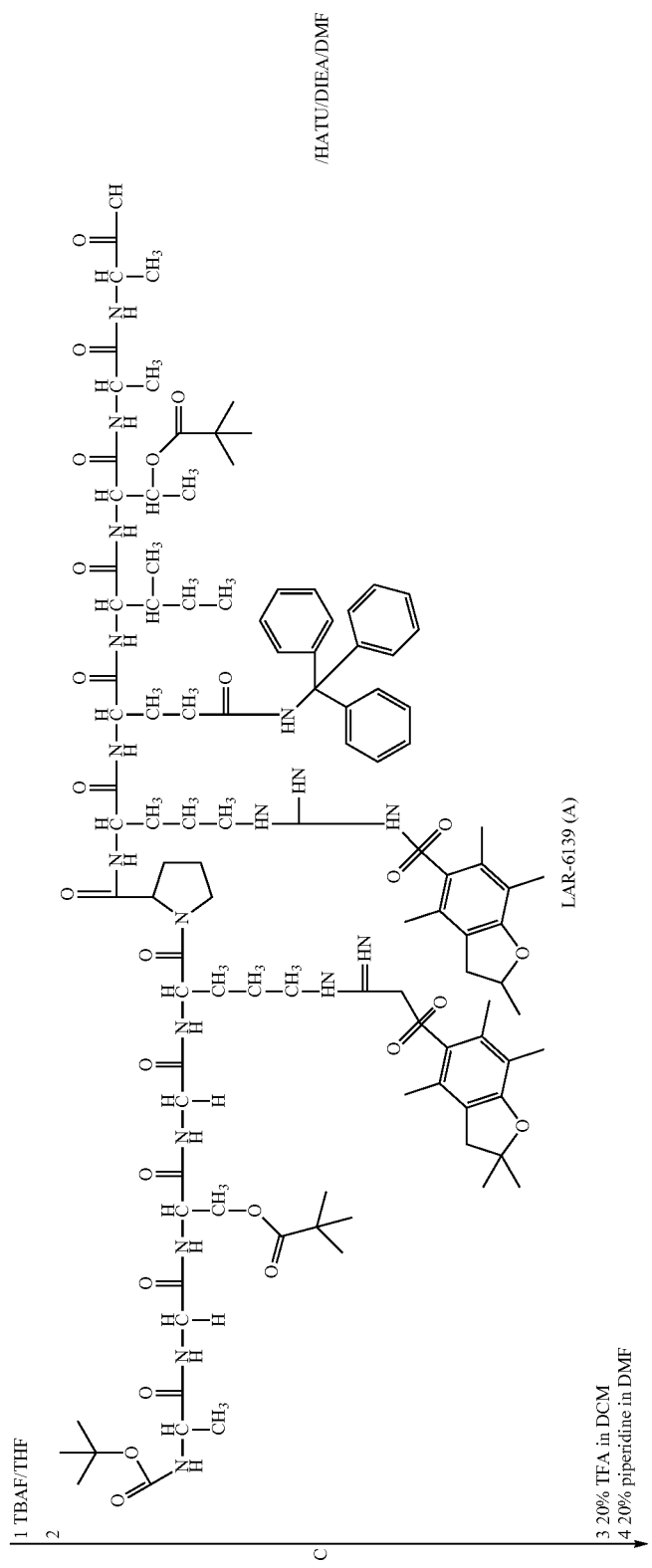

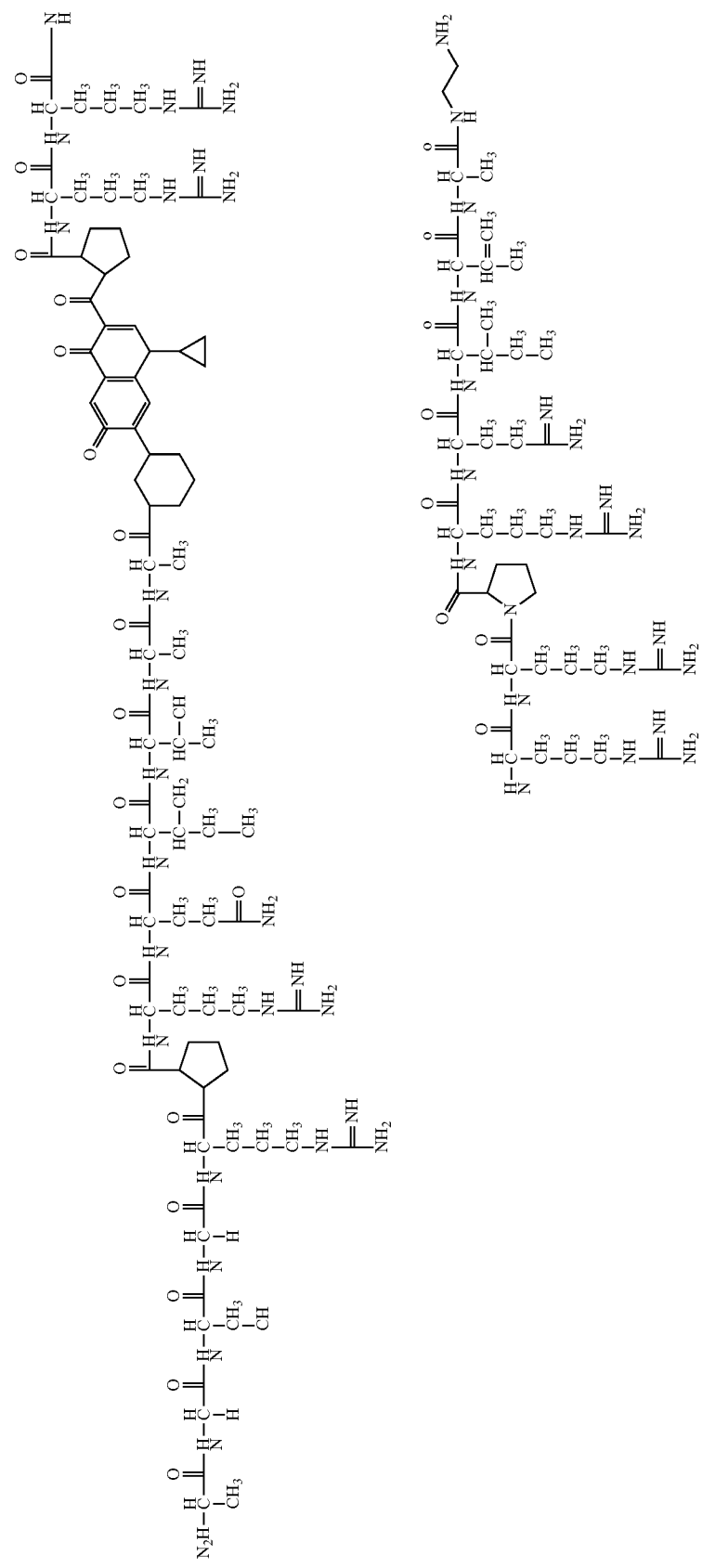

Example 15

Preparation of LAR-7022-CIPRO-LAR-7023

The compound was prepared in the same manner as EXAMPLE 14. This produced 15 mg (60%) of the desired product ($R_f$=0.15 in 20% methanol, 1.0% Acetic acid in Chloroform). MALDI-TOF MS: Calculated for $C_{114}H_{176}FN_{35}O_{36}$: 2631.83 amu. found 2631.92.

Example 16

Preparation of LAR-7022-CIPRO-LAR-7024

The compound was prepared in the same manner as EXAMPLE 14. This produced 50 mg (96%) of the desired product ($R_f$=0.15 in 20% methanol, 1.0% Acetic acid in Chloroform). MALDI-TOF MS: Calculated for $C_{96}H_{150}FN_{29}O_{33}$: 2257.39 amu. found 2257.65.

Example 17

Preparation of LAR-7041-CIPRO-LAR-7043

The compound was prepared in the same manner as EXAMPLE 14. This produced 20 mg (80%) of the desired product ($R_f$=0.15 in 20% methanol, 1.0% Acetic acid in Chloroform). MALDI-TOF MS: Calculated for $C_{123}H_{182}FN_{29}O_{21}$: 2627.93 amu. found 2627.98

Example 18

Synthesis of a Bioactive Polymer Responsive to Up-Regulated Inflammatory Peptidases THDI/PCL/Si—OH/Cipro is an example of pharmaceutically active polyurethane containing 5% of drugs according to the invention. The conditions of synthesis for this reaction are as follows.

0.8 grams of PCL and 0.56 grams of alkyl hyrdroxyl terminate silicone are reacted with 0.16 mL of THDI in the presence of 30 µl of the catalyst, dibutyltin dilaurate, in a nitrogen atmosphere with in dimethylsulfoxide (DMSO) (6 mL) for one hour. The reaction temperature is maintained between 60-70° C. 0.67 grams of LAR-6139-CIPRO-LAR-7009 is dissolved in 3 ml DMSO was then added into reaction system. The reaction is keep at 60-70° C. for 5 hours and then at room temperature for overnight. Reaction is finally stopped with 1 ml of methanol. The final drug polymer is precipitated in a mixture of ether/water (50 v/v %). The precipitated polymer is then dissolved in acetone and precipitated in ether again. This washing procedure is repeated three times.

Ciprofloxacin is the only component in the drug polymer which has a strong detectable absorbance at 280 nm in the UV range. Hence, its presence can be detected using a UV detector. Figure 5 super-imposes the UV chromatogram for the drug polymer with its universal gel permeation chromatography (GPC) curves using a universal refractive index detector. The latter detects the presence of all molecules because it has a dependence on mass of material present, eluting out of the GPC column at a specific time. Hence, a comparison of the two signals shows that the distribution of ciprofloxacin is identical to the distribution of actual molecular weight chains, meaning that there was no preferential coupling of norfloxacin/ciprofloxacin to low versus high molecular weight chains or vice-versa; implies that the coupling of ciprofloxacin was uniform.

Example 19

Synthesis of a Bioactive Polymer Responsive to Excreted Microbial Peptidases The compound was prepared in the same manner as EXAMPLE 18 except LAR-7022-CIPRO-LAR-7023 was used as chain extender.

Example 20

Synthesis of a Bioactive Polymer Responsive to Excreted Microbial Peptidases The compound was prepared in the same manner as EXAMPLE 18 except LAR-7022-CIPRO-LAR-7024 was used as chain extender.

Example 21

Synthesis of a Bioactive Polymer Responsive to Excreted Fungal Peptidases

The compound was prepared in the same manner as EXAMPLE 18 except LAR-7041-CIPRO-LAR-7043 was used as chain extender.

Biology

Example 22

MMP-9 Bioresponsive Degradation Assay

The hydrolysis of the substrates were done in MMPs activation buffer. The buffer contains 15 mM Tris-HCl, Ph 7.4, 150 mM NaCl, 1 mM $CaCl_2$, and 1 mM APMA (4-aminophenylmercuric acetate). 100 nM MPP-9 was added in this activating buffer and incubated at 37° C. for 4 hr. to activate enzyme. After activating, the 1 mM substrates were added to be hydrolysis at room temperature for 3 hr. Degradation of LAR-7009 ((β-ala-gly-ser-gly-arg-pro-arg-gln-ile-thr-ala-ala): 1408.85 amu produced specific fragment pick: 1121.66 corresponding to PRRRRPRQ sequence.

Example 23

Staphopain A and B Bioresponsive Degradation Assay

The hydrolysis of the substrates were done in staphopain buffer. This buffer contains 50 mM Tris-HCl, pH 7.4, 2 mM cysteine, 0.001% (w/v) CHAPS, 5 mM EDTA. 100 nM staphopain and 1 µM substrate were added in the buffer, incubated at room temperature for 2 hr. Degradation of LAR-7022 (b-ADDIG-TSRPQE): 1188.56 amu produced specific fragment pick: 717.37 corresponding to TSRPQE sequence.

Example 24

Aureolysin Bioresponsive Degradation Assay

The hydrolysis of the substrate was performed in aureolysin activation buffer. The buffer contains 100 mM Tris-HCL, 1 mM $CaCL_2$, pH 7.8, and 1 mM 3,4-dichloroisoumarine. 100 nM aureolysin and 1 mM substrate were added in the buffer, and then incubated at 37° C. for 3 hr.

Example 25

V₈ Proteinase Bioresponsive Degradation Assay

The hydrolysis of the substrate was performed in V₈ proteinase activation buffer. The buffer contains 100 mM Tris-HCL, 1 mM $CaCl_2$, pH 7.8, and 10 mM o-phenanthroline. 100 nM V₈ proteinase and 1 mM substrate were added in the buffer, and then incubated at 37° C. for 3 hr.

Example 26

SAP Bioresponsive Degradation Assay

Reconstitution of SAP was performed through the dissolving the lyophilized powder into 200 µl of distill water, so that the final concentration at 1.0 mg/ml in 10 mM sodium citrate buffer, pH6.0. The hydrolysis was performed in 100 mM sodium acetate buffer, pH 3.3. 100 nM SAP and 1 µM substrate were added in the reaction buffer, and incubated at 37° C. for 3 hours.

Example 27

Carboxypeptidase Bioresponsive Degradation Assay

The hydrolysis of the substrate was performed in carboxypeptidase buffer. The buffer contains 25 mM Tris-HCL, 100 mM NaCl, pH 7.6. The hydrolysis was performed by adding 100 nM carboxypeptidase and 1 µM substrate in this buffer at 25° C. for 1 hour.

Example 28

Aminopeptidase P Bioresponsive Degradation Assay

The hydrolysis of the substrate was performed in aminopeptidase P buffer. The buffer contains 100 mM potassium phosphate, 10 mM EDTA, 5% Glycerol and 5 mM DTT, pH 8.0. Immediately before use, the enzyme solution was made. This solution contains 10 mg sold/ml cold buffer. Added 1 µM substrate in 1 ml buffer and incubated at 37° C. for 1 hour.

Example 29

Degradation of P-CIPRO-P by Peptidase Enzymes

Degradation of P-CIPRO-P by up-regulated peptidases was measured as described in Examples 30-32. The results, provided in Table 5, show that ciprofloxacin is released in the presence of enzymes, but not in the absence of enzymes.

TABLE 5

Ciprofloxacin released from P-CIPRO-P

| P-CIPRO-P | Enzymes Employed | Ciprofloxacin Released (ng/mL) | |
|---|---|---|---|
| | | No Enzyme Treatment | Enzyme Treatment |
| LAR-6139-CIPRO-LAR-7009 | MMP-9, Aminopeptidase N, Aminopeptidase P; Carboxypeptidase A | 0.00 | 897.68 |
| LAR-7022-CIPRO-7023 | Staphopain A, B, Aureolysin, Aminopeptidase P; D-ala-D-ala carboxypeptidase A | 0.00 | 993.78 |
| LAR-7041-CIPRO-7043 | SAP1, SAP2, SAP3, Aminopeptidase P, Carboxypeptidase B | 0.00 | 287.37 |

Example 30

Degradation of P-CIPRO-P by Up-Regulated Inflammatory Peptidases

The commercial human MMP-9 is proenzyme of MMP-9 at 88 KDa. Activation of proenzyme MMP-9 was added commercial MMP-9 in activating buffer (15 mM Tris-HCl, pH 7.4, 150 mM NaCl, 1 mM $CaCl_2$, and 1 mM 4-aminophenylmercuric acetate) final concentration at 100 µM.

1 mM substrate of LAR-6139-CIPRO-LAR-7009 was dissolved in 15 mM Tris-HCl pH 7.4, 150 mM NaCl buffer. Degradation was initially by adding 1 uL carboxypeptidase B (100 µM), 1 µL aminopeptidase P (3.5 mM), and 1 µL activated MMP-9. Incubation proceeded at room temperature for 3 hours, and then at 37° C. for 1 hour. The amount of ciprofloxacin release was conducted by quantitative HPLC.

Example 31

Degradation of P-CIPRO-P by Secreted Microbial Peptidases

LAR-7022-CIPRO-LAR-7023 or LAR-7022-CIPRO-LAR-7024 was dissolved in 25 mM Tris-HCl pH 7.4 final concentrations of both peptides at 1 µM. Degradation was initially by adding 1 µL staphopain (100 µM) then incubating at room temperature for 2 hours. After initial incubation, degradation system pH was adjusted up to pH 8.0. Degradation was restarted by adding 1 µL of aureolysin (100 µM), aminopeptidase (3.5 mM), and pyrrolidinone carboxypeptidase (100 µM). Incubation proceeded at 37° C. incubator for 3 hours. The amount of ciprofloxacin release was conducted by quantitative HPLC.

Example 32

Degradation of P-CIPRO-P by Excreted Fungal Peptidases

LAR-7041-CIPRO-LAR-7043 dissolved in 1 mL 100 mM sodium acetate pH 3.3 final concentrations at 1 µM. Degradation was initially by adding 1 µL 100 µM SAP stock, 1 µL 100 µM carboxypeptidase B, and 1 µL 100 µM aminopeptidase P. Incubation proceeded at 37° C. for 3 hours. The amount of ciprofloxacin release was conducted by quantitative HPLC.

Example 33

Degradation of Bioresponsive Polymers by Peptidase Enzymes

Degradation of polymer incorporating a polyamide responsive to up-regulated peptidases was measured as described in Examples 34-37. The results, provided in Table 6, show that ciprofloxacin is release in the presence of enzymes, but not in the absence of enzymes. Furthermore, the release of ciprofloxacin is halted if up-regulated peptidases are removed from the buffer, and returns after up-regulated peptidases are returned to the buffer.

TABLE 6

Ciprofloxacin Released from Bioresponsive Polymer

| Bioresponsive Polymer | Ciprofloxacin Released (ng/mL) | | | |
|---|---|---|---|---|
| | First "ON" | Second "OFF" | Third "ON" | Fourth "OFF" |
| Infla_polymer (LAR-6139-CIPRO-LAR-7009) | 123.70 | 0.00 | 136.71 | 0.00 |
| Bact_polymer (LAR-7022-CIPRO-LAR-7023) | 97.99 | 0.00 | 99.70 | 0.00 |
| Fung_polymer (LAR-7041-CIPRO-LAR-7043) | 153.89 | 0.00 | 180.67 | 0.00 |

Example 34

Degradation of Polymer Incorporating Polyamide Responsive to Up-Regulated Inflammatory Peptidases The hydrolysis was conducted in the same manner as EXAMPLE 30 ensuring that concentration of P-Cipro-P remains at 1 nM. This is estimated from concentration of P-Cipro-P incorporated into the polymer. This is derived from UV measurements of polymer to determine the amount of ciprofloxacin present in the polymer backbone. The incubation proceeded at 37° C. for 3 hours. The amount of ciprofloxacin release was conducted by quantitative HPLC.

Example 35

Degradation of Polymer Incorporating Polyamide Responsive to Excreted Microbial Peptidases The hydrolysis was conducted in the same manner as EXAMPLE 31 ensuring that concentration of P-Cipro-P remains at 1 mM. This is estimated from concentration of P-Cipro-P incorporated into the polymer. This is derived from UV measurements of polymer to determine the amount of ciprofloxacin present in the polymer backbone. The incubation proceeded at 37° C. for 5 hours. The amount of ciprofloxacin release was conducted by quantitative HPLC.

Example 36

Degradation of Polymer Incorporating Polyamide Responsive to Excreted Fungal Peptidases The hydrolysis was conducted in the same manner as EXAMPLE 32 ensuring that concentration of P-Cipro-P remains at 1 mM. This is estimated from concentration of P-Cipro-P incorporated into the polymer. This is derived from UV measurements of polymer to determine the amount of ciprofloxacin present in the polymer backbone. The incubation proceeded at 37° C. for 5 hours. The amount of ciprofloxacin release was conducted by quantitative HPLC.

Example 37

ON-OFF-ON Responsiveness of Polymer Incorporating Polyamide Responsive to Up-Regulated Peptidases The establishment of ON is conducted in the same manner as described by EXAMPLE 30. The OFF position is established by incubating substrate with the enzyme buffer system described in the same example. Between system changeovers three washes with buffer is conducted. ON-OFF-ON-OFF responsiveness measurements were conducted using inflammatory peptidases, microbial peptidases, and fungal peptidases as provided in Examples 34-37. The results are provided in Table 6.

Example 38

Control Systems

All control degradation profiles was conducted as outlined in EXAMPLE 22 through EXAMPLE 26 utilizing the control peptides VFFRRQTA and PRRICV, identified as LAR-7047 and LAR-7048 respectively, as substrates. No degradation was observed in these systems.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A polymer of formula II:

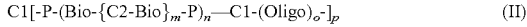

C1[-P-(Bio-{C2-Bio}$_m$-P)$_n$—C1-(Oligo)$_o$-]$_p$     (II)

wherein (i) each Bio is, independently, one or more biologically active agents, or precursors thereof, tethered to polyamide linker P through hydrolysable covalent bonds;

(ii) each P is a polyamide linker susceptible to hydrolysis by a peptidase enzyme and tethered to said Bio and C1; and (iii) C1 is a coupling segment linking P to Oligo, wherein C1 is formed from a silicone diol;

(iv) C2 is a polyamide linker susceptible to hydrolysis by a peptidase enzyme linking Bio to Bio;

(v) Oligo is a short length of polymer segment having a molecular weight of less than 5,000 and comprising less than 100 monomeric repeating units; wherein each of n, o, and p is independently an integer greater than 0; and m is an integer 0 or 1;

wherein said polyamide linker comprises an amino acid sequence selected from the group consisting of:

β-Ala-gly-ser-gly-arg-pro-arg-gln-ile-thr-ala-ala (SEQ ID NO. 4);

Pro-arg-arg-arg-arg-pro-arg-gln-ile-thr-ala (SEQ ID NO. 6);

β-ala-asp-asp-ile-gly-thr-ser-arg-pro-gln-glu (SEQ ID NO. 8);

Phe-ala-ala-gly-ile-gly-thr-ser-arg-pro-gln (SEQ ID NO. 10);

Gly-gly-gly-gly-gly-ala-leu-leu-glu (SEQ ID NO. 12);

β-ala-gly-lys-pro-ala-leu-phe-phe-arg-leu (SEQ ID NO. 13);

β-ala-ser-leu-ala-ser-pro-pro-thr-ser-leu-val-phe (SEQ ID NO. 15);

Gly-lys-pro-ala-leu-phe-phe-ala-leu (SEQ ID NO. 17); and

β-ala-lys-leu-arg-phe-ser-lys-gln-glu-asp-asp (SEQ ID NO. 19).

2. The polymer of claim 1, wherein each P is an independent polyamide linker comprising 60 or fewer amino acids.

3. The polymer of claim 1, wherein said Bio is one or more biologically-active entities selected from the group consisting of carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, vitamins, lipids, and prodrugs thereof.

4. The polymer of claim 1, wherein Oligo comprises polyurethane, polyurea, polyamides, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polytetramethylene oxide, or polyethylenebutylene segments.

5. A composition comprising the polymer of claim 1 blended with a compatible base polymer.

6. The composition of claim 5, wherein said base polymer is selected from the group consisting of polyurethanes, polysulfones, polycarbonates, polyesters, polyethylene, polypropylene, polystyrene, polysilicone, poly(acrylonitrile-butadienestyrene), polybutadiene, polyisoprene, polymethylmethacrylate, polyamine, polyvinylacetate, polyacrylonitrile, polyvinyl chloride, polyethylene, terephthalate, cellulose and other polysaccharides.

7. A shaped article comprising the composition of claim 5.

8. A shaped article comprising the polymer of claim 1.

9. The shaped article of claim 8, wherein said shaped article is in the form of an implantable medical device, self-supporting film, or fiber.

10. The shaped article of claim 9, wherein said article is an implantable medical device selected from the group consisting of a cardiac-assist device, a catheter, a stent, a prosthetic implant, a suture, a cuff, a mesh, a hernia patch, a wound dressing, a bandage, an artificial sphincter, and a drug delivery device.

11. The polymer of claim 1, wherein each P, independently, comprises an amino acid sequence selected from the group consisting of:

β-Ala-gly-ser-gly-arg-pro-arg-gln-ile-thr-ala-ala (SEQ ID NO. 4);

Pro-arg-arg-arg-arg-pro-arg-gln-ile-thr-ala (SEQ ID NO. 6);

β-ala-asp-asp-ile-gly-thr-ser-arg-pro-gln-glu (SEQ ID NO. 8);

Phe-ala-ala-gly-ile-gly-thr-ser-arg-pro-gln (SEQ ID NO. 10);

Gly-gly-gly-gly-gly-ala-leu-leu-glu (SEQ ID NO. 12);

β-ala-gly-lys-pro-ala-leu-phe-phe-arg-leu (SEQ ID NO. 13); and

Gly-lys-pro-ala-leu-phe-phe-ala-leu (SEQ ID NO. 17).

12. The polymer of claim 1, wherein said Bio is an antibiotic.

13. The polymer of claim 12, wherein said Bio is formed from ciprofloxacin.

14. The polymer of claim 1, wherein Oligo comprises a polyester.

15. The polymer of claim 14, wherein Oligo comprises poly-caprolactone.

16. The polymer of claim 4, wherein said polymer comprises a moiety —P-Bio-P—, wherein Bio is ciprofloxacin, a P comprises the sequence β-Ala-gly-ser-gly-arg-pro-arg-gln-ile-thr-ala-ala (SEQ ID NO. 4), and the second P comprises the sequence Pro-arg-arg-arg-arg-pro-arg-aln-ile-thr-ala (SEQ ID NO. 6).

17. The polymer of claim 4, wherein said polymer comprises a moiety —P-Bio-P—, wherein Bio is ciprofloxacin, a P comprises the sequence β-ala-asp-asp-ile-gly-thr-ser-arg-pro-gln-glu (SEQ ID NO. 8), and the second P comprises the sequence Phe-ala-ala-gly-ile-gly-thr-ser-arg-pro-gln (SEQ ID NO. 10).

18. The polymer of claim 4, wherein said polymer comprises a moiety —P-Bio-P—, wherein Bio is ciprofloxacin, a P comprises the sequence β-ala-asp-asp-ile-gly-thr-ser-arg-pro-gln-glu (SEQ ID NO. 8), and the second P comprises the sequence Gly-gly-gly-gly-gly-ala-leu-leu-glu (SEQ ID NO. 12).

19. The polymer of claim 4, wherein said polymer comprises a moiety —P-Bio-P—, wherein Bio is ciprofloxacin, a P comprises the sequence β-ala-gly-lys-pro-ala-leu-phe-phe-arg-leu (SEQ ID NO. 13), and the second P comprises the sequence Gly-lys-pro-ala-leu-phe-phe-ala-leu (SEQ ID NO. 17).

* * * * *

SEQUENCE LISTING

<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Val Phe Phe Arg Arg Gln Thr Ala
1               5

```
<210> SEQ ID NO 2
<211> LENGTH: 6
<212> TYPE: PRT
<213> ORGANISM: Artificial Sequence
<220> FEATURE:
<223> OTHER INFORMATION: Synthetic Construct

<400> SEQUENCE: 2

Pro Arg Arg Ile Cys Val
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Ala Gly Ser Gly Arg Pro Arg Gln Ile Thr Ala Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Ala Gly Ser Gly Arg Pro Arg Gln Ile Thr Ala Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Pro Arg Arg Arg Arg Pro Arg Gln Ile Thr Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Pro Arg Arg Arg Arg Pro Arg Gln Ile Thr Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Ala Asp Asp Ile Gly Thr Ser Arg Pro Gln Glu
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Ala Asp Asp Ile Gly Thr Ser Arg Pro Gln Glu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Phe Ala Ala Gly Ile Gly Thr Ser Arg Pro Gln
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Phe Ala Ala Gly Ile Gly Thr Ser Arg Pro Gln
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Gly Gly Gly Gly Gly Ala Leu Leu Glu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Gly Ala Leu Leu Glu
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Ala Gly Lys Pro Ala Leu Phe Phe Arg Leu
1               5                   10

```
<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

Ala Ser Leu Ala Ser Pro Pro Thr Ser Leu Val Phe
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

Ala Ser Leu Ala Ser Pro Pro Thr Ser Leu Val Phe
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Gly Lys Pro Ala Leu Phe Phe Ala Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Gly Lys Pro Ala Leu Phe Phe Ala Leu
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Ala Lys Leu Arg Phe Ser Lys Gln Glu Asp Asp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Ala Lys Leu Arg Phe Ser Lys Gln Glu Asp Asp
1               5                   10

<210> SEQ ID NO 20
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Lys Leu Arg Phe Ser Lys Gln Glu Asp Asp
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 21

Lys Xaa Pro Gly Ser Lys Gln Glu Asp Asp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Lys Pro Xaa Gly Ser Lys Gln Glu Asp Asp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Ser Leu Ala Ser Pro Pro Thr Ser Leu Val Phe
1               5                   10
```